US012773268B2

(12) United States Patent
Zoubi et al.

(10) Patent No.: US 12,773,268 B2
(45) Date of Patent: Oct. 27, 2026

(54) GAP FINDER INDEX FOR HIGH POWER SHORT DURATION (HPSD) RF LESIONS

(71) Applicant: Biosense Webster (Israel) Ltd., Yokneam (IL)

(72) Inventors: Alaa Zoubi, Sakhnin (IL); Muhammad Khatib, Yafa an-Naseriyye (IL); Ofer Klemm, Koranit (IL); Erez Silberschein, Tel Aviv (IL); Meir Bar-Tal, Halfa (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 334 days.

(21) Appl. No.: 18/524,199

(22) Filed: Nov. 30, 2023

(65) Prior Publication Data

US 2024/0189032 A1 Jun. 13, 2024

Related U.S. Application Data

(60) Provisional application No. 63/430,979, filed on Dec. 7, 2022.

(51) Int. Cl.
*A61B 18/00* (2006.01)
*A61B 18/14* (2006.01)
(Continued)

(52) U.S. Cl.
CPC .......... *A61B 34/10* (2016.02); *A61B 18/1492* (2013.01); *G16H 50/20* (2018.01);
(Continued)

(58) Field of Classification Search
CPC . A61B 34/10; A61B 2034/104; A61B 5/4848; A61B 2034/105; G16H 50/20; G06N 20/00
See application file for complete search history.

(56) References Cited

U.S. PATENT DOCUMENTS 10,588,692 B2 3/2020 Saba et al.
2013/0102862 A1 4/2013 Mercader et al.
(Continued)

FOREIGN PATENT DOCUMENTS

EP 1956992 A2 8/2008
EP 1922005 B1 12/2011
(Continued)

OTHER PUBLICATIONS

International Search Report and Written Opinion issued on Mar. 11, 2024 mailed for PCT Patent Application No. PCT/IB2023/062240.

*Primary Examiner* — Jaymi E Della
(74) *Attorney, Agent, or Firm* — Clayton, McKay & Bailey, PC

(57) ABSTRACT

A method is described herein. The method is implemented by an optimization engine executed by a processor. The optimization engine receives data that includes performance metrics of mapping and ablation procedures. In turn, the optimization generates procedure expected outcomes for the mapping and ablation procedures based on the data and success predictions for a current ablation procedure utilizing the procedure expected outcomes. The gap index is calculated. The optimization engine, also, outputs an ablation recommendation based on the success predictions and the gap index.

22 Claims, 14 Drawing Sheets

(51) Int. Cl.
*A61B 34/10* (2016.01)
*G16H 50/20* (2018.01)

(52) U.S. Cl.
CPC ............... *A61B 2018/00375* (2013.01); *A61B 2018/00577* (2013.01); *A61B 2018/00714* (2013.01); *A61B 2018/00839* (2013.01); *A61B 2018/00904* (2013.01); *A61B 2034/104* (2016.02)

(56) References Cited

U.S. PATENT DOCUMENTS

| | | | | |
|---|---|---|---|---|
| 2018/0221075 | A1* | 8/2018 | Warner | A61B 18/12 |
| 2020/0060757 | A1* | 2/2020 | Ben-Haim | A61B 34/10 |
| 2022/0183669 | A1 | 6/2022 | Bar-tal et al. | |

FOREIGN PATENT DOCUMENTS

| | | | |
|---|---|---|---|
| EP | 3936070 | A1 | 1/2022 |
| EP | 3944808 | A1 | 2/2022 |
| EP | 3951790 | A1 | 2/2022 |
| EP | 3967258 | A1 | 3/2022 |
| WO | 2007063443 | A2 | 6/2007 |
| WO | 2012092275 | A1 | 7/2012 |
| WO | 2018130976 | A1 | 7/2018 |

* cited by examiner

GAP FINDER INDEX FOR HIGH POWER SHORT DURATION (HPSD) RF LESIONS

CROSS REFERENCE TO RELATED APPLICATIONS

This application claims the benefit of U.S. Provisional Application No. 63/430,979 filed Dec. 7, 2022, which is incorporated by reference as if fully set forth.

FIELD OF INVENTION

The disclosure herein is related to a gap finder index for radiofrequency (RF) lesions. The gap finder index may be applied in high power short duration (HPSD), for example. The gap finder index may be applied to other energy sources, such as cyro and pulsed-field ablation (sometimes referred to as PFA or interchangeably as irreversible electroporation (IRE)), that are delivered intra-cardially.

BACKGROUND

A pulmonary vein isolation (PVI) procedure includes ablating a series of neighboring locations on the PV so as to produce a ring or line of ablated tissue. If the procedure is successful, the ablation ring or line acts as a barrier to transmission of an electric wave. However, the rate for creating successful rings can be improved—recent data suggests that approximately 21% of 179 cases of certain Very high-power short-duration temperature-controlled ablation procedures found gaps in the barrier after a first pass of ring creation.

The present method for checking for a successful procedure, such as a first pass isolation criteria, includes manually searching for gaps in the ring or line, such as the distance between ablation indications, such as the indications provided by the VISITAG™ module from Biosense Webster, Inc. (the indications being referred to herein as "VisiTags"), by cardiac signal mapping. As would be understood cardiac signal mapping is provided as an example, and any other verification method for a block may be used. This, taken together with the poor first pass success rate, is not always reliable and is time consuming for physicians performing the ablations.

SUMMARY

According to an exemplary embodiment, a method is provided. The method is implemented by an optimization engine executed by one or more processors. The method includes receiving data including performance metrics of mapping and ablation procedures, generating procedure expected outcomes for the mapping and ablation procedures based on the data, generating one or more success predictions for a current ablation procedure utilizing the procedure expected outcomes, calculating a gap index for the performed ablation, and outputting an ablation recommendation based on the one or more success predictions including the gap index. The present method for checking for a successful procedure, such as a first pass isolation criteria, includes manually searching for gaps in the ring or line, such as the distance between VisiTags, by cardiac signal mapping. As would be understood, cardiac signal mapping is provided as an example, and any other verification method for a block may be used.

According to one or more embodiments, the exemplary method embodiment above can be implemented as an apparatus, a system, and/or a computer program product.

BRIEF DESCRIPTION OF THE DRAWINGS

A more detailed understanding may be had from the following description, given by way of example in conjunction with the accompanying drawings, wherein like reference numerals in the figures indicate like elements, and wherein.

DETAILED DESCRIPTION

A system and method for utilizing a gap finder index for high power short duration (HPSD) rf lesions are provided. The system and method may be implemented with a computer. The system and method may include an input/out (I/O) device for receiving data from a catheter configured to perform ablation on a patient heart. The system and method may include a memory and processor acting operably to perform the method including processing the received data. The system and method include receiving, by an optimization engine executed by one or more processors, data including performance metrics of mapping and ablation procedures, generating, by the optimization engine, procedure expected outcomes for the mapping and ablation procedures based on the data, generating, by the optimization engine, one or more success predictions for a current ablation procedure utilizing the procedure expected outcomes, performing an ablation and calculating a gap index of the ablation, and outputting the gap index of the ablation. The performing an ablation may include ablating a series of neighboring locations to produce a ring or line of ablated tissue. The performed ablation may include providing one or more ablations to prevent transmission of an electric wave. The one or more success predictions may include searching for gaps in an ablation ring or ablation line. The higher the gap index the higher a probability of a gap in the ablation. The data may include at least an ablation index derived from at least one of force, power and time of ablation of a site. The data may include at least an average or maximum temperature of the ablation of a site. The data may include at least a quality of stability derived from a site stability algorithm. The data may include at least a distance to the nearest stable site using a site stability algorithm. The gap index of the ablation may be a function of at least the ablation index, an average temperature of the ablation, a quality of stability, and a distance to the nearest stable site. The gap index may be calculated for each location an ablation is performed. The system and method may include outputting a map of ablation sites highlighting ablation locations with a high gap index. A high gap index may be determined by thresholding the gap index.

Figure 1:
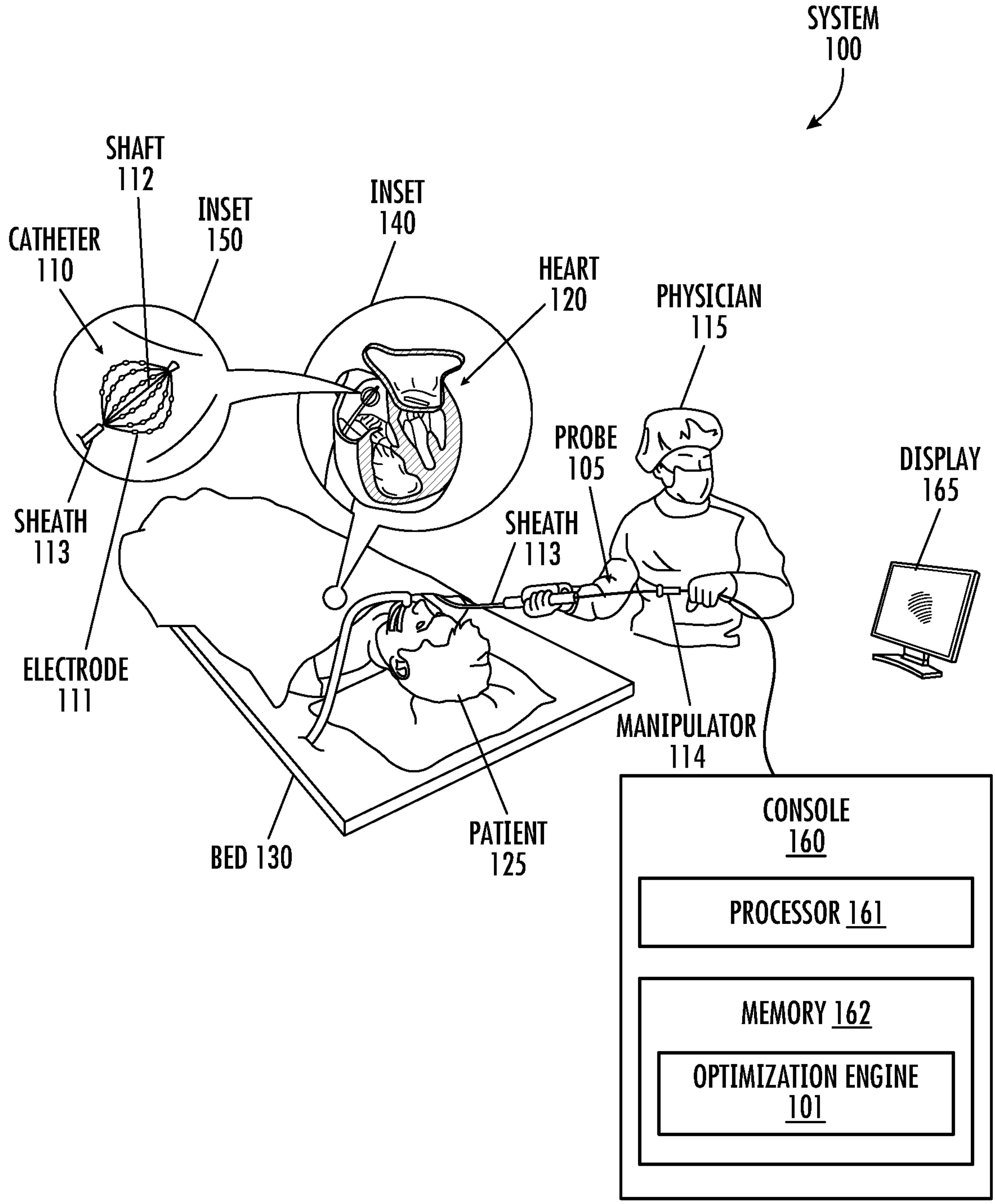
FIG. 1 illustrates a diagram of an exemplary system in which one or more features of the disclosure subject matter can be implemented according to one or more embodiments.

FIG. 1 is a diagram of an example system (e.g., medical device equipment), shown as a system 100, in which one or more features of the subject matter herein can be implemented according to one or more embodiments. All or part of the system 100 can be used to collect information (e.g., data/inputs, such as biometric data and/or a training dataset) and/or used to implement an optimization engine 101 (e.g., a ML/AI algorithm or model thereof). The optimization engine 101 can be defined as an optimization in which model parameters that best fit data and prior statistical knowledge are estimated in an iterative process to identify ablation gaps and predict success.

The system 100, as illustrated, includes a probe 105 with a catheter 110 (including at least one electrode 111), a shaft 112, a sheath 113, and a manipulator 114. The system 100, as illustrated, also includes a physician 115 (or a medical professional, technician, clinician, etc.), a heart 120, a patient 125, and a bed 130 (or a table). Insets 140 and 150 show the heart 120 and the catheter 110 in greater detail. The system 100 also, as illustrated, includes a console 160 (including one or more processors 161 and memories 162) and a display 165. Each element and/or item of the system 100 is representative of one or more of that element and/or that item. The example of the system 100 shown in FIG. 1 can be modified to implement the embodiments disclosed herein. The disclosed embodiments can similarly be applied using other system components and settings. Additionally, the system 100 can include additional components, such as elements for sensing electrical activity, wired or wireless connectors, processing and display devices, or the like.

The system 100 can be utilized to detect, diagnose, and/or treat cardiac conditions (e.g., using the optimization engine 101). Cardiac conditions, such as cardiac arrhythmias, persist as common and dangerous medical ailments, especially in the aging population. For instance, the system 100 can be part of a surgical system (e.g., CARTO® system sold by Biosense Webster) that is configured to obtain biometric data (e.g., anatomical and electrical measurements of a patient's organ, such as the heart 120) and perform a cardiac ablation procedure. According to one or more embodiments, the biometric data can include anatomical and electrical measurements acquired in a significant portion of an atrium during the mapping and ablation procedures More particularly, treatments for cardiac conditions such as cardiac arrhythmia often require obtaining a detailed mapping of cardiac tissue, chambers, veins, arteries and/or electrical pathways. For example, a prerequisite for performing a catheter ablation (as described herein) successfully is that the cause of the cardiac arrhythmia is accurately located in a chamber of the heart 120. Such locating may be done via an electrophysiological investigation during which electrical potentials are detected spatially resolved with a mapping catheter (e.g., the catheter 110) introduced into the chamber of the heart 120. This electrophysiological investigation, the so-called electro-anatomical mapping, thus provides 3D mapping data which can be displayed on a monitor. In many cases, the mapping function and a treatment function (e.g., ablation) are provided by a single catheter or group of catheters such that the mapping catheter also operates as a treatment (e.g., ablation) catheter at the same time. In this case, the optimization engine 101 can be directly stored and executed by the catheter 110.

In patients (e.g., the patient 125) with normal sinus rhythm (NSR), the heart (e.g., the heart 120), which includes atrial, ventricular, and excitatory conduction tissue, is electrically excited to beat in a synchronous, patterned fashion. This electrical excitement can be detected as intracardiac electrocardiogram (IC ECG) data or the like.

In patients (e.g., the patient 125) with a cardiac arrhythmia (e.g., atrial fibrillation or aFib), abnormal regions of cardiac tissue do not follow a synchronous beating cycle associated with normally conductive tissue, which is in contrast to patients with NSR. Instead, the abnormal regions of cardiac tissue aberrantly conduct to adjacent tissue, thereby disrupting the cardiac cycle into an asynchronous cardiac rhythm. This asynchronous cardiac rhythm can also be detected as the IC ECG data. Such abnormal conduction has been previously known to occur at various regions of the heart 120, for example, in the region of the sino-atrial (SA) node, along the conduction pathways of the atrioventricular (AV) node, or in the cardiac muscle tissue forming the walls of the ventricular and atrial cardiac chambers. There are other conditions, such as flutter, where the pattern of abnormally conducting tissues lead to reentry paths such that the chamber beats in a regular pattern that can be multiple times the sinus rhythm.

In support of the system 100 detecting, diagnosing, and/or treating cardiac conditions, the probe 105 can be navigated by the physician 115 into the heart 120 of the patient 125 lying on the bed 130. For instance, the physician 115 can insert the shaft 112 through the sheath 113, while manipulating a distal end of the shaft 112 using the manipulator 114 near the proximal end of the catheter 110 and/or deflection from the sheath 113. As shown in an inset 140, the catheter 110 can be fitted at the distal end of the shaft 112. The catheter 110 can be inserted through the sheath 113 in a collapsed state and can be then expanded within the heart 120.

Generally, electrical activity at a point in the heart 120 may be typically measured by advancing the catheter 110 containing an electrical sensor at or near its distal tip (e.g., the at least one electrode 111) to that point in the heart 120, contacting the tissue with the sensor and acquiring data at that point. One drawback with mapping a cardiac chamber using a catheter type containing only a single, distal tip electrode is the long period of time required to accumulate data on a point-by-point basis over the requisite number of points required for a detailed map of the chamber as a whole. Accordingly, multiple-electrode catheters (e.g., the catheter 110) have been developed to simultaneously measure electrical activity at multiple points in the heart chamber.

The catheter 110, which can include the at least one electrode 111 and a portion coupled onto a body thereof, can be configured to obtain biometric data, such as electrical signals of an intra-body organ (e.g., the heart 120), and/or to ablate tissue areas of thereof (e.g., a cardiac chamber of the heart 120). The electrodes 111 are representative of any like elements, such as tracking coils, piezoelectric transducer, electrodes, or combination of elements configured to ablate the tissue areas or to obtain the biometric data. According to one or more embodiments, the catheter 110 can include one or more position sensors that used are to determine trajectory information. The trajectory information, as well as other information including force data and temperature sensors, for example, can be used to infer motion characteristics, such as the contractility of the tissue.

Biometric data (e.g., patient biometrics, patient data, or patient biometric data) can include one or more of local activation times (LATs), electrical activity, topology, bipolar mapping, reference activity, ventricle activity, dominant frequency, impedance, or the like. The LAT can be a point in time of a threshold activity corresponding to a local activation, calculated based on a normalized initial starting point. Electrical activity can be any applicable electrical signals that can be measured based on one or more thresholds and can be sensed and/or augmented based on signal to noise ratios and/or other filters. A topology can correspond to the physical structure of a body part or a portion of a body part and can correspond to changes in the physical structure relative to different parts of the body part or relative to different body parts. A dominant frequency can be a frequency or a range of frequency that is prevalent at a portion of a body part and can be different in different portions of the same body part. For example, the dominant frequency of a PV of a heart can be different than the dominant frequency of the right atrium of the same heart. Impedance can be the resistance measurement at a given area of a body part.

Examples of biometric data include, but are not limited to, patient identification data, IC ECG data, bipolar intracardiac reference signals, anatomical and electrical measurements, trajectory information, body surface (BS) ECG data, historical data, brain biometrics, blood pressure data, ultrasound signals, radio signals, audio signals, a two- or three-dimensional image data, blood glucose data, and temperature data. The biometrics data can be used, generally, to monitor, diagnosis, and treatment any number of various diseases, such as cardiovascular diseases (e.g., arrhythmias, cardiomyopathy, and coronary artery disease) and autoimmune diseases (e.g., type I and type II diabetes). BS ECG data can include data and signals collected from electrodes on a surface of a patient, IC ECG data can include data and signals collected from electrodes within the patient, and ablation data can include data and signals collected from tissue that has been ablated. Further, BS ECG data, IC ECG data, and ablation data, along with catheter electrode position data, can be derived from one or more procedure recordings.

For example, the catheter 110 can use the electrodes 111 to implement intravascular ultrasound and/or MRI catheterization to image the heart 120 (e.g., obtain and process the biometric data). Inset 150 shows the catheter 110 in an enlarged view, inside a cardiac chamber of the heart 120. Although the catheter 110 is shown to be a point catheter, it will be understood that any shape that includes one or more electrodes 111 can be used to implement the exemplary embodiments disclosed herein.

Examples of the catheter 110 include, but are not limited to, a linear catheter with multiple electrodes, a balloon catheter including electrodes dispersed on multiple spines that shape the balloon, a lasso or loop catheter with multiple electrodes, a contact-force sensing catheter, or any other applicable shape or type. Linear catheters can be fully or partially elastic such that it can twist, bend, and or otherwise change its shape based on received signal and/or based on application of an external force (e.g., cardiac tissue) on the linear catheter. The balloon catheter can be designed such that when deployed into a patient's body, its electrodes can be held in intimate contact against an endocardial surface. As would be understood, while a balloon catheter is described to aid in understanding the invention, a spherical or grid-shaped catheter or a catheter with multiple spines may also be used. As an example, a balloon catheter can be inserted into a lumen, such as a PV. The balloon catheter can be inserted into the PV in a deflated state, such that the balloon catheter does not occupy its maximum volume while being inserted into the PV. The balloon catheter can expand while inside the PV, such that those electrodes on the balloon catheter are in contact with an entire circular section of the PV. Such contact with an entire circular section of the PV, or any other lumen, can enable efficient imaging and/or ablation.

According to other examples, body patches and/or body surface electrodes may also be positioned on or proximate to a body of the patient 125. The catheter 110 with the one or more electrodes 111 can be positioned within the body (e.g., within the heart 120) and a position of the catheter 110 can be determined by the system 100 based on signals transmitted and received between the one or more electrodes 111 of the catheter 110 and the body patches and/or body surface electrodes. Additionally, the electrodes 111 can sense the biometric data from within the body of the patient 125, such as within the heart 120 (e.g., the electrodes 111 sense the electrical potential of the tissue in real time). The biometric data can be associated with the determined position of the catheter 110 such that a rendering of the patient's body part (e.g., the heart 120) can be displayed and show the biometric data overlaid on a shape of the body part.

The probe 105 and other items of the system 100 can be connected to the console 160. The console 160 can include any computing device, which employs the ML/AI algorithm or model (represented as the optimization engine 101). According to an exemplary embodiment, the console 160 includes the one or more processors 161 (any computing hardware) and the memory 162 (any non-transitory tangible media), where the one or more processors 161 execute computer instructions with respect the optimization engine 101 and the memory 162 stores these instructions for execution by the one or more processors 161. For instance, the console 160 can be configured to receive and/or store the biometric data on a database of the memory 162, process the biometric data, and determine if a given tissue area conducts electricity.

According to one or more embodiments, the console 160 can be further programmed by the optimization engine 101 (in software) to carry out the functions of receiving data including performance metrics of mapping and ablation procedures, generating procedure expected outcomes for the mapping and ablation procedures based on the data, generating success predictions for a current ablation procedure, and outputting a probability for a redo procedure based on the success prediction. In this regard, the optimization engine 101 can include, implement, and/or incorporate an unsupervised and/or supervised ML/AI algorithm (described herein with respect to FIGS. 3 and 6). In generating expected outcomes for the mapping and ablation procedures, the present system and method operate using the various measured data collected during the procedure to categorize the outcome based on known data from other procedures. In this way the system and method, via optimization engine 101, utilizing the ablation index and its associated parameters as described below, predicts the outcome of the ablation procedure. In this way, the system and method may indicate to a medical professional or identify on the display of the system that additional corrective actions need be taken in order to improve the success of the procedure. One such addition action may be to reperform the ablation.

Generally, the optimization engine 101 can provide one or more user interfaces, such as on behalf of the operating system or other application and/or directly as needed. The user interfaces include, but are not limited to, internet browsers, graphic user interfaces (GUIs), window interfaces, and/or other visual interfaces for applications, operating systems, file folders, and the like. According to one or more embodiments, the optimization engine 101 can be external to the console 160 and can be located, for example, in the catheter 110, in an external device, in a mobile device, in a cloud-based device, or can be a standalone processor. In this regard, the optimization engine 101 can be transferable/downloaded in electronic form, over a network.

In an example, the console 160 can be any computing device, as noted herein, including software (e.g., the optimization engine 101) and/or hardware (e.g., the processor 161 and the memory 162), such as a general-purpose computer, with suitable front end and interface circuits for transmitting and receiving signals to and from the probe 105, as well as for controlling the other components of the system 100. For example, the front end and interface circuits include input/output (I/O) communication interfaces that enables the console 160 to receive signals from and/or transfer signals to the at least one electrode 111. The console 160 can include real-time noise reduction circuitry typically configured as a field programmable gate array (FPGA), followed by an analog-to-digital (A/D) ECG or electrocardiograph/electromyogram (EMG) signal conversion integrated circuit. The console 160 can pass the signal from an A/D ECG or EMG circuit to another processor and/or can be programmed to perform one or more functions disclosed herein.

The display 165, which can be any electronic device for the visual presentation of the biometric data, is connected to the console 160. According to an exemplary embodiment, during a procedure, the console 160 can facilitate on the display 165 a presentation of a body part rendering to the physician 115 and store data representing the body part rendering in the memory 162. For instance, maps depicting motion characteristics can be rendered/constructed based on the trajectory information sampled at a sufficient number of points in the heart 120. As an example, the display 165 can include a touchscreen that can be configured to accept inputs from the physician 115, in addition to presenting the body part rendering.

In some embodiments, the physician 115 can manipulate the elements of the system 100 and/or the body part rendering using one or more input devices, such as a touch pad, a mouse, a keyboard, a gesture recognition apparatus, or the like. For example, an input device can be used to change a position of the catheter 110, such that rendering is updated. The display 165 can be located at a same location or a remote location, such as a separate hospital or in separate healthcare provider networks.

According to one or more embodiments, the system 100 can also obtain the biometric data using ultrasound, computed tomography (CT), MRI, or other medical imaging techniques utilizing the catheter 110 or other medical equipment. For instance, the system 100 can obtain ECG data and/or anatomical and electrical measurements of the heart 120 (e.g., the biometric data) using one or more catheters 110 or other sensors. More particularly, the console 160 can be connected, by a cable, to BS electrodes, which include adhesive skin patches affixed to the patient 125. The BS electrodes can procure/generate the biometric data in the form of the BS ECG data. For instance, the processor 161 can determine position coordinates of the catheter 110 inside the body part (e.g., the heart 120) of the patient 125. The position coordinates may be based on impedances or electromagnetic fields measured between the body surface electrodes and the electrode 111 of the catheter 110 or other electromagnetic components. Additionally, or alternatively, location pads, which generate magnetic fields used for navigation, may be located on a surface of the bed 130 and may be separate from the bed 130. The biometric data can be transmitted to the console 160 and stored in the memory 162. Alternatively, or in addition, the biometric data may be transmitted to a server, which may be local or remote, using a network as further described herein.

According to one or more exemplary embodiments, the catheter 110 may be configured to ablate tissue areas of a cardiac chamber of the heart 120. Inset 150 shows the catheter 110 in an enlarged view, inside a cardiac chamber of the heart 120. For instance, ablation electrodes, such as the at least one electrode 111, may be configured to provide energy to tissue areas of an intra-body organ (e.g., the heart 120). The energy may be thermal energy and may cause damage to the tissue area starting from the surface of the tissue area and extending into the thickness of the tissue area. The biometric data with respect to ablation procedures (e.g., ablation tissues, ablation locations, etc.) can be considered ablation data.

According to an example, with respect to obtaining the biometric data, a multi-electrode catheter (e.g., the catheter 110) can be advanced into a chamber of the heart 120. Anteroposterior (AP) and lateral fluorograms can be obtained to establish the position and orientation of each of the electrodes. ECGs can be recorded from each of the electrodes 111 in contact with a cardiac surface relative to a temporal reference, such as the onset of the P-wave in sinus rhythm from a BS ECG and/or signals from electrodes 111 of the catheter 110 placed in the coronary sinus. The system, as further disclosed herein, may differentiate between those electrodes that register electrical activity and those that do not due to absence of close proximity to the endocardial wall. After initial ECGs are recorded, the catheter may be repositioned, and fluorograms and ECGs may be recorded again. An electrical map (e.g., via cardiac mapping) can then be constructed from iterations of the process above.

Cardiac mapping can be implemented using one or more techniques. Generally, mapping of cardiac areas such as cardiac regions, tissue, veins, arteries and/or electrical pathways of the heart 120 may result in identifying problem areas such as scar tissue, arrhythmia sources (e.g., electric rotors), healthy areas, and the like. Cardiac areas may be mapped such that a visual rendering of the mapped cardiac areas is provided using a display, as further disclosed herein. Additionally, cardiac mapping (which is an example of heart imaging) may include mapping based on one or more modalities such as, but not limited to LAT, local activation velocity, an electrical activity, a topology, a bipolar mapping, a dominant frequency, or an impedance. Data (e.g., biometric data) corresponding to multiple modalities may be captured using a catheter (e.g., the catheter 110) inserted into a patient's body and may be provided for rendering at the same time or at different times based on corresponding settings and/or preferences of the physician 115.

As an example of a first technique, cardiac mapping may be implemented by sensing an electrical property of heart tissue, for example, LAT, as a function of the precise location within the heart 120. The corresponding data (e.g., biometric data) may be acquired with one or more catheters (e.g., the catheter 110) that are advanced into the heart 120 and that have electrical and location sensors (e.g., the electrodes 111) in their distal tips. As specific examples, location and electrical activity may be initially measured on about 10 to about 20 points on the interior surface of the heart 120. These data points may be generally sufficient to generate a preliminary reconstruction or map of the cardiac surface to a satisfactory quality. The preliminary map may be combined with data taken at additional points to generate a more comprehensive map of the heart's electrical activity. In clinical settings, it is not uncommon to accumulate data at 100 or more sites (e.g., several thousand) to generate a detailed, comprehensive map of heart chamber electrical activity. The generated detailed map may then serve as the basis for deciding on a therapeutic course of action, for example, tissue ablation as described herein, to alter the propagation of the heart's electrical activity and to restore normal heart rhythm.

Further, cardiac mapping can be generated based on detection of intracardiac electrical potential fields (e.g., which is an example of IC ECG data and/or bipolar intracardiac reference signals). A non-contact technique to simultaneously acquire a large amount of cardiac electrical information may be implemented. For example, a catheter type having a distal end portion may be provided with a series of sensor electrodes distributed over its surface and connected to insulated electrical conductors for connection to signal sensing and processing means. The size and shape of the end portion may be such that the electrodes are spaced substantially away from the wall of the cardiac chamber. Intracardiac potential fields may be detected during a single cardiac beat. According to an example, the sensor electrodes may be distributed on a series of circumferences lying in planes spaced from each other. These planes may be perpendicular to the major axis of the end portion of the catheter. At least two additional electrodes may be provided adjacent at the ends of the major axis of the end portion. As a more specific example, the catheter may include four circumferences with eight electrodes spaced equiangularly on each circumference. Accordingly, in this specific implementation, the catheter may include at least 34 electrodes (32 circumferential and 2 end electrodes). As another more specific example, the catheter may include other multi-spline catheters, such as five soft flexible branches, eight radial splines, or a parallel splined pancake turner type (e.g., any of which may have a total of 42 electrodes).

As example of electrical or cardiac mapping, an electrophysiological cardiac mapping system and technique based on a non-contact and non-expanded multi-electrode catheter (e.g., the catheter 110) can be implemented. ECGs may be obtained with one or more catheters 110 having multiple electrodes (e.g., such as between 42 to 122 electrodes). According to this implementation, knowledge of the relative geometry of the probe and the endocardium can be obtained by an independent imaging modality, such as transesophageal echocardiography. After the independent imaging, non-contact electrodes may be used to measure cardiac surface potentials and construct maps therefrom (e.g., in some cases using bipolar intracardiac reference signals). This technique can include the following steps (after the independent imaging step): (a) measuring electrical potentials with a plurality of electrodes disposed on a probe positioned in the heart 120; (b) determining the geometric relationship of the probe surface and the endocardial surface and/or other reference; (c) generating a matrix of coefficients representing the geometric relationship of the probe surface and the endocardial surface; and (d) determining endocardial potentials based on the electrode potentials and the matrix of coefficients.

As another example of electrical or cardiac mapping, a technique and apparatus for mapping the electrical potential distribution of a heart chamber can be implemented. An intra-cardiac multi-electrode mapping catheter assembly can be inserted into the heart 120. The mapping catheter (e.g., the catheter 110) assembly can include a multi-electrode array with one or more integral reference electrodes (e.g., one or the electrodes 111) or a companion reference catheter.

According to one or more exemplary embodiments, the electrodes may be deployed in the form of a substantially spherical array, which may be spatially referenced to a point on the endocardial surface by the reference electrode or by the reference catheter this is brought into contact with the endocardial surface. The preferred electrode array catheter may carry a number of individual electrode sites (e.g., at least 24). Additionally, this example technique may be implemented with knowledge of the location of each of the electrode sites on the array, as well as knowledge of the cardiac geometry. These locations are preferably determined by a technique of impedance plethysmography.

In view of electrical or cardiac mapping and according to another example, the catheter 110 can be a heart mapping catheter assembly that may include an electrode array defining a number of electrode sites. The heart mapping catheter assembly can also include a lumen to accept a reference catheter having a distal tip electrode assembly that may be used to probe the heart wall. The map heart mapping catheter assembly can include a braid of insulated wires (e.g., having 24 to 64 wires in the braid), and each of the wires may be used to form electrode sites. The heart mapping catheter assembly may be readily positionable in the heart 120 to be used to acquire electrical activity information from a first set of non-contact electrode sites and/or a second set of in-contact electrode sites.

Further, according to another example, the catheter 110 that can implement mapping electrophysiological activity within the heart can include a distal tip that is adapted for delivery of a stimulating pulse for pacing the heart or an ablative electrode for ablating tissue in contact with the tip. This catheter 110 can further include at least one pair of orthogonal electrodes to generate a difference signal indicative of the local cardiac electrical activity adjacent the orthogonal electrodes.

As noted herein, the system 100 can be utilized to detect, diagnose, and/or treat cardiac conditions. In example operation, a process for measuring electrophysiologic data in a heart chamber may be implemented by the system 100. The process may include, in part, positioning a set of active and passive electrodes into the heart 120, supplying current to the active electrodes, thereby generating an electric field in the heart chamber, and measuring the electric field at the passive electrode sites. The passive electrodes are contained in an array positioned on an inflatable balloon of a balloon catheter. In preferred embodiments, the array is said to have from 60 to 64 electrodes.

As another example operation, cardiac mapping may be implemented by the system 100 using one or more ultrasound transducers. The ultrasound transducers may be inserted into a patient's heart 120 and may collect a plurality of ultrasound slices (e.g., two dimensional or three-dimensional slices) at various locations and orientations within the heart 120. The location and orientation of a given ultrasound transducer may be known and the collected ultrasound slices may be stored such that they can be displayed at a later time. One or more ultrasound slices corresponding to the position of the probe 105 (e.g., a treatment catheter shown as catheter 110) at the later time may be displayed and the probe 105 may be overlaid onto the one or more ultrasound slices.

In view of the system 100, it is noted that cardiac arrhythmias, including atrial arrhythmias, may be of a multiwavelet reentrant type, characterized by multiple asynchronous loops of electrical impulses that are scattered about the atrial chamber and are often self-propagating (e.g., another example of the IC ECG data). Alternatively, or in addition to the multiwavelet reentrant type, cardiac arrhythmias may also have a focal origin, such as when an isolated region of tissue in an atrium fires autonomously in a rapid, repetitive fashion (e.g., another example of the IC ECG data). Ventricular tachycardia (V-tach or VT) is a tachycardia, or fast heart rhythm that originates in one of the ventricles of the heart. This is a potentially life-threatening arrhythmia because it may lead to ventricular fibrillation and sudden death.

For example, aFib occurs when the normal electrical impulses (e.g., another example of the IC ECG data) generated by the sinoatrial node are overwhelmed by disorganized electrical impulses (e.g., signal interference) that originate in the atria veins and PVs causing irregular impulses to be conducted to the ventricles. An irregular heartbeat results and may last from minutes to weeks, or even years. aFib is often a chronic condition that leads to a small increase in the risk of death often due to strokes. A line of treatment for aFib is medication that either slows the heart rate or revert the heart rhythm back to normal. Additionally, persons with aFib are often given anticoagulants to protect them from the risk of stroke. The use of such anticoagulants comes with its own risk of internal bleeding. In some patients, medication is not sufficient and their aFib is deemed to be drug-refractory, i.e., untreatable with standard pharmacological interventions. Synchronized electrical cardioversion may also be used to convert aFib to a normal heart rhythm. Alternatively, aFib patients are treated by catheter ablation.

A catheter ablation-based treatment may include mapping the electrical properties of heart tissue, especially the endocardium and the heart volume, and selectively ablating cardiac tissue by application of energy. Electrical or cardiac mapping (e.g., implemented by any electrophysiological cardiac mapping system and technique described herein) includes creating a map of electrical potentials (e.g., a voltage map) of the wave propagation along the heart tissue or a map of arrival times (e.g., a LAT map) to various tissue located points. Electrical or cardiac mapping (e.g., a cardiac map) may be used for detecting local heart tissue dysfunction. Ablations, such as those based on cardiac mapping, can cease or modify the propagation of unwanted electrical signals from one portion of the heart 120 to another.

The ablation process damages the unwanted electrical pathways by formation of non-conducting lesions. Various energy delivery modalities have been disclosed for forming lesions, and include use of microwave, laser and more commonly, radiofrequency energies to create conduction blocks along the cardiac tissue wall. Another example of an energy delivery technique includes pulsed-field ablation (PFA) to effect irreversible electroporation (IRE)by providing pulsed high-voltage electric fields that damage cell membranes. In a two-step procedure (e.g., mapping followed by ablation) electrical activity at points within the heart 120 is typically sensed and measured by advancing the catheter 110 containing one or more electrical sensors (e.g., electrodes 111) into the heart 120 and obtaining/acquiring data at a multiplicity of points (e.g., as biometric data generally, or as ECG data specifically). This ECG data is then utilized to select the endocardial target areas, at which ablation is to be performed.

Cardiac ablation and other cardiac electrophysiological procedures have become increasingly complex as clinicians treat challenging conditions such as atrial fibrillation and ventricular tachycardia. The treatment of complex arrhythmias can now rely on the use of three-dimensional (3D) mapping systems to reconstruct the anatomy of the heart chamber of interest. In this regard, the optimization engine 101 employed by the system 100 herein manipulates and evaluates the biometric data generally, or the ECG data specifically, to produce improved tissue data that enables more accurate diagnosis, images, scans, and/or maps for treating an abnormal heartbeat or arrhythmia. For example, cardiologists rely upon software, such as the Complex Fractionated Atrial Electrograms (CFAE) module of the CARTO® 3 3D mapping system, produced by Biosense Webster, Inc. (Diamond Bar, Calif.), to generate and analyze ECG data. The optimization engine 101 of the system 100 enhances this software to generate and analyze the improved biometric data, which further provide multiple pieces of information regarding electrophysiological properties of the heart 120 (including the scar tissue) that represent cardiac substrates (anatomical and functional) of aFib.

Accordingly, the system 100 can implement a 3D mapping system, such as CARTO® 3 3D mapping system, to localize the potential arrhythmogenic substrate of the cardiomyopathy in terms of abnormal ECG detection. The substrate linked to these cardiac conditions is related to the presence of fragmented and prolonged ECGs in the endocardial and/or epicardial layers of the ventricular chambers (right and left). For instance, areas of low or medium voltage may exhibit ECG fragmentation and prolonged activities. Further, during sinus rhythm, areas of low or medium voltage may corresponds to a critical isthmus identified during sustained and organized ventricular arrhythmias (e.g., applies to non-tolerated ventricular tachycardias, as well as in the atria). In general, abnormal tissue is characterized by low-voltage ECGs. However, initial clinical experience in endo-epicardial mapping indicates that areas of low-voltage are not always present as the sole arrhythmogenic mechanism in such patients. In fact, areas of low or medium voltage may exhibit ECG fragmentation and prolonged activities during sinus rhythm, which corresponds to the critical isthmus identified during sustained and organized ventricular arrhythmias, e.g., applies only to non-tolerated ventricular tachycardias. Moreover, in many cases, ECG fragmentation and prolonged activities are observed in the regions showing a normal or near-normal voltage amplitude (>1-1.5 mV). Although the latter areas may be evaluated according to the voltage amplitude, they cannot be considered as normal according to the intracardiac signal, thus representing a true arrhythmogenic substrate. The 3D mapping may be able to localize the arrhythmogenic substrate on the endocardial and/or epicardial layer of the right/left ventricle, which may vary in distribution according to the extension of the main disease.

As another example operation, cardiac mapping may be implemented by the system 100 using one or more multiple-electrode catheters (e.g., the catheter 110). Multiple-electrode catheters are used to stimulate and map electrical activity in the heart 120 and to ablate sites of aberrant electrical activity. In use, the multiple-electrode catheter is inserted into a major vein or artery, e.g., femoral vein, and then guided into the chamber of the heart 120 of concern. A typical ablation procedure involves the insertion of the catheter 110 having at least one electrode 111 at its distal end, into a heart chamber. A reference electrode is provided, taped to the skin of the patient or by means of a second catheter that is positioned in or near the heart or selected from one or the other electrodes 111 of the catheter 110. Radio frequency (RF) current is applied to a tip electrode 111 of the ablating catheter 110, and current flows through the media that surrounds it (e.g., blood and tissue) toward the reference electrode. The distribution of current depends on the amount of electrode surface in contact with the tissue as compared to blood, which has a higher conductivity than the tissue. Heating of the tissue occurs due to its electrical resistance. The tissue is heated sufficiently to cause cellular destruction in the cardiac tissue resulting in formation of a lesion within the cardiac tissue which is electrically non-conductive. During this process, heating of the tip electrode 111 also occurs as a result of conduction from the heated tissue to the electrode itself. If the electrode temperature becomes sufficiently high, possibly above 60 degrees Celsius, a thin transparent coating of dehydrated blood protein can form on the surface of the electrode 111. If the temperature continues to rise, this dehydrated layer can become progressively thicker resulting in blood coagulation on the electrode surface. Because dehydrated biological material has a higher electrical resistance than endocardial tissue, impedance to the flow of electrical energy into the tissue also increases. If the impedance increases sufficiently, an impedance rise occurs, and the catheter 110 must be removed from the body and the tip electrode 111 cleaned.

Figure 2:
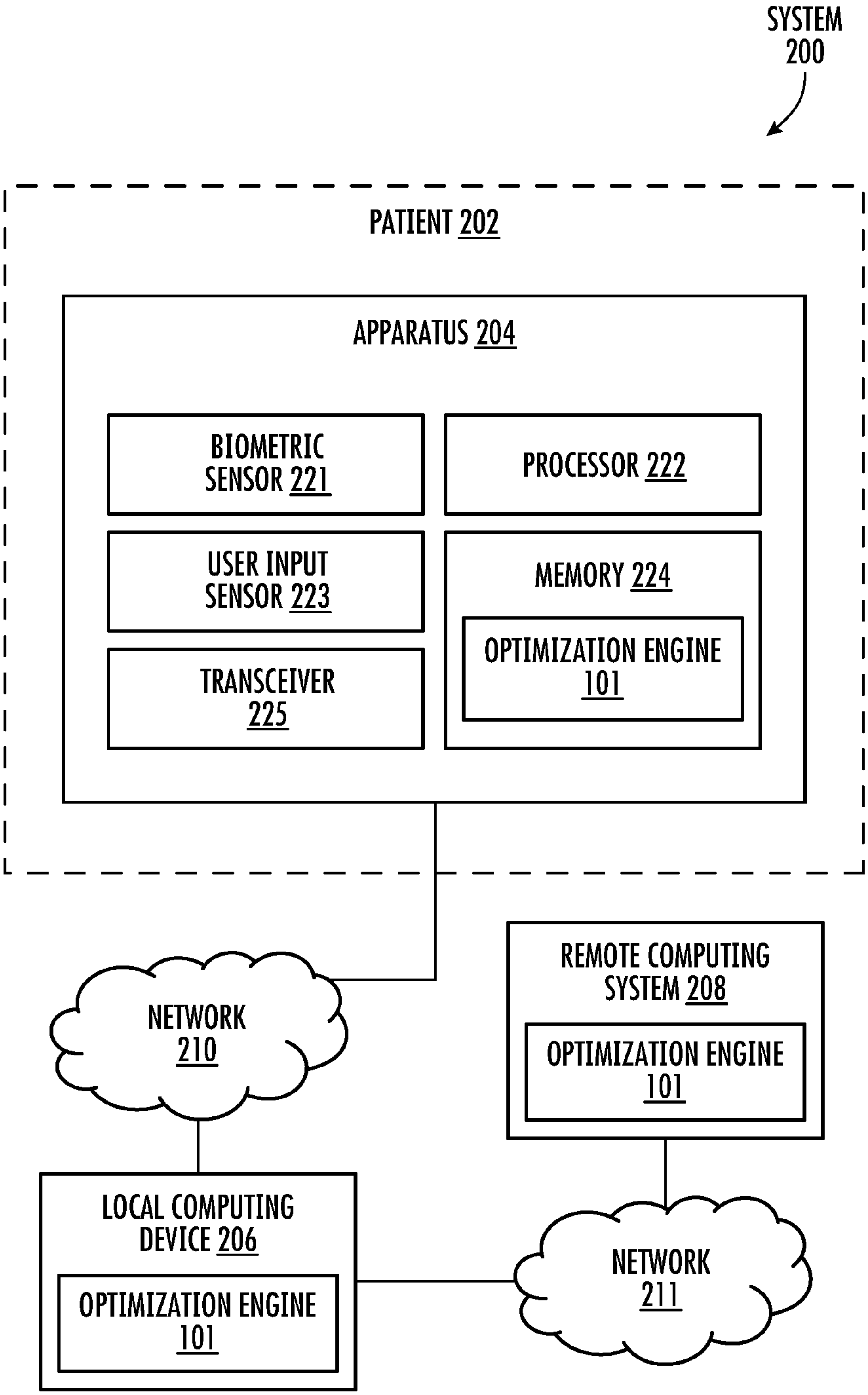
FIG. 2 illustrates a block diagram of an example system for an anatomically correct reconstruction of an atrium according to one or more embodiments.

FIG. 2 illustrates a diagram of a system 200 in which one or more features of the disclosure subject matter can be implemented is illustrated according to one or more exemplary embodiments. The system 200 includes, in relation to a patient 202 (e.g., an example of the patient 125 of FIG. 1), an apparatus 204, a local computing device 206, a remote computing system 208, a first network 210, and a second network 211. Further, the apparatus 204 can include a biometric sensor 221 (e.g., an example of the catheter 110 of FIG. 1), a processor 222, a user input (UI) sensor 223, a memory 224, and a transceiver 225. The optimization engine 101 of FIG. 1 is reused in FIG. 2 for ease of explanation and brevity.

According to an embodiment, the apparatus 204 can be an example of the system 100 of FIG. 1, where the apparatus 204 can include both components that are internal to the patient and components that are external to the patient. According to another embodiment, the apparatus 204 can be an apparatus that is external to the patient 202 that includes an attachable patch (e.g., that attaches to a patient's skin). According to another embodiment, the apparatus 204 can be internal to a body of the patient 202 (e.g., subcutaneously implantable), where the apparatus 204 can be inserted into the patient 202 via any applicable manner including orally injecting, surgical insertion via a vein or artery, an endoscopic procedure, or a laparoscopic procedure. According to an embodiment, while a single apparatus 204 is shown in FIG. 2, example systems may include a plurality of apparatuses.

Accordingly, the apparatus 204, the local computing device 206, and/or the remote computing system 208 can be programed to execute computer instructions with respect the optimization engine 101. As an example, the memory 223 stores these instructions for execution by the processor 222 so that the apparatus 204 can receive and process the biometric data via the biometric sensor 201. In this way, the processor 222 and the memory 223 are representative of processors and memories of the local computing device 206 and/or the remote computing system 208.

The apparatus 204, local computing device 206, and/or the remote computing system 208 can be any combination of software and/or hardware that individually or collectively store, execute, and implement the optimization engine 101 and functions thereof. Further, the apparatus 204, local computing device 206, and/or the remote computing system 208 can be an electronic, computer framework comprising and/or employing any number and combination of computing device and networks utilizing various communication technologies, as described herein. The apparatus 204, local computing device 206, and/or the remote computing system 208 can be easily scalable, extensible, and modular, with the ability to change to different services or reconfigure some features independently of others.

The networks 210 and 211 can be a wired network, a wireless network, or include one or more wired and wireless networks. According to an embodiment, the network 210 is an example of a short-range network (e.g., local area network (LAN), or personal area network (PAN)). Information can be sent, via the network 210, between the apparatus 204 and the local computing device 206 using any one of various short-range wireless communication protocols, such as Bluetooth, Wi-Fi, Zigbee, Z-Wave, near field communications (NFC), ultra-band, Zigbee, or infrared (IR). Further, the network 211 is an example of one or more of an Intranet, a local area network (LAN), a wide area network (WAN), a metropolitan area network (MAN), a direct connection or series of connections, a cellular telephone network, or any other network or medium capable of facilitating communication between the local computing device 206 and the remote computing system 208. Information can be sent, via the network 211, using any one of various long-range wireless communication protocols (e.g., TCP/IP, HTTP, 3G, 4G/LTE, or 5G/New Radio). For either network 210 and 211 wired connections can be implemented using Ethernet, Universal Serial Bus (USB), RJ-11 or any other wired connection and wireless connections can be implemented using Wi-Fi, WiMAX, and Bluetooth, infrared, cellular networks, satellite or any other wireless connection methodology.

In operation, the apparatus 204 can continually or periodically obtain, monitor, store, process, and communicate via network 210 the biometric data associated with the patient 202. Further, the apparatus 204, local computing device 206, and/ the remote computing system 208 are in communication through the networks 210 and 211 (e.g., the local computing device 206 can be configured as a gateway between the apparatus 204 and the remote computing system 208). For instance, the apparatus 204 can be an example of the system 100 of FIG. 1 configured to communicate with the local computing device 206 via the network 210. The local computing device 206 can be, for example, a stationary/standalone device, a base station, a desktop/laptop computer, a smart phone, a smartwatch, a tablet, or other device configured to communicate with other devices via networks 211 and 210. The remote computing system 208, implemented as a physical server on or connected to the network 211 or as a virtual server in a public cloud computing provider (e.g., Amazon Web Services (AWS)®) of the network 211, can be configured to communicate with the local computing device 206 via the network 211. Thus, the biometric data associated with the patient 202 can be communicated throughout the system 200.

Elements of the apparatus 204 are now described. The biometric sensor 221 may include, for example, one or more transducers configured to convert one or more environmental conditions into an electrical signal, such that different types of biometric data are observed/obtained/acquired. For example, the biometric sensor 221 can include one or more of an electrode (e.g., the electrode 111 of FIG. 1), a temperature sensor (e.g., thermocouple), a blood pressure sensor, a blood glucose sensor, a blood oxygen sensor, a pH sensor, an accelerometer, and a microphone.

The processor 222, in executing the optimization engine 101, can be configured to receive, process, and manage the biometric data acquired by the biometric sensor 221, and communicate the biometric data to the memory 224 for storage (e.g., on a database therein) and/or across the network 210 via the transceiver 225 (e.g., to a database thereof). Biometric data from one or more other apparatuses 204 can also be received by the processor 222 through the transceiver 225. Also, as described in more detail herein, the processor 222 may be configured to respond selectively to different tapping patterns (e.g., a single tap or a double tap) received from the UI sensor 223, such that different tasks of a patch (e.g., acquisition, storing, or transmission of data) can be activated based on the detected pattern. In some embodiments, the processor 222 can generate audible feedback with respect to detecting a gesture.

The UI sensor 223 includes, for example, a piezoelectric sensor or a capacitive sensor configured to receive a user input, such as a tapping or touching. For example, the UI sensor 223 can be controlled to implement a capacitive coupling, in response to tapping or touching a surface of the apparatus 204 by the patient 202. Gesture recognition may be implemented via any one of various capacitive types, such as resistive capacitive, surface capacitive, projected capacitive, surface acoustic wave, piezoelectric and infrared touching. Capacitive sensors may be disposed at a small area or over a length of the surface, such that the tapping or touching of the surface activates the monitoring device.

The memory 224 is any non-transitory tangible media, such as magnetic, optical, or electronic memory (e.g., any suitable volatile and/or non-volatile memory, such as random-access memory or a hard disk drive). The memory 224 stores the computer instructions for execution by the processor 222.

The transceiver 225 may include a separate transmitter and a separate receiver. Alternatively, the transceiver 225 may include a transmitter and receiver integrated into a single device.

In operation, the apparatus 204, utilizing the optimization engine 101, observes/obtains the biometric data of the patient 202 via the biometric sensor 221, stores the biometric data in the memory, and shares this biometric data across the system 200 via the transceiver 225. The optimization engine 101 can then utilize models, algorithms (e.g., the unsupervised and/or supervised ML/AI algorithm), neural network to identify ablation gaps and provide success predictions to the physician 1515 to transform operations the system 100 that raise a success probability for a next procedure and/or eliminate unnecessary subsequent procedures.

Figure 3:
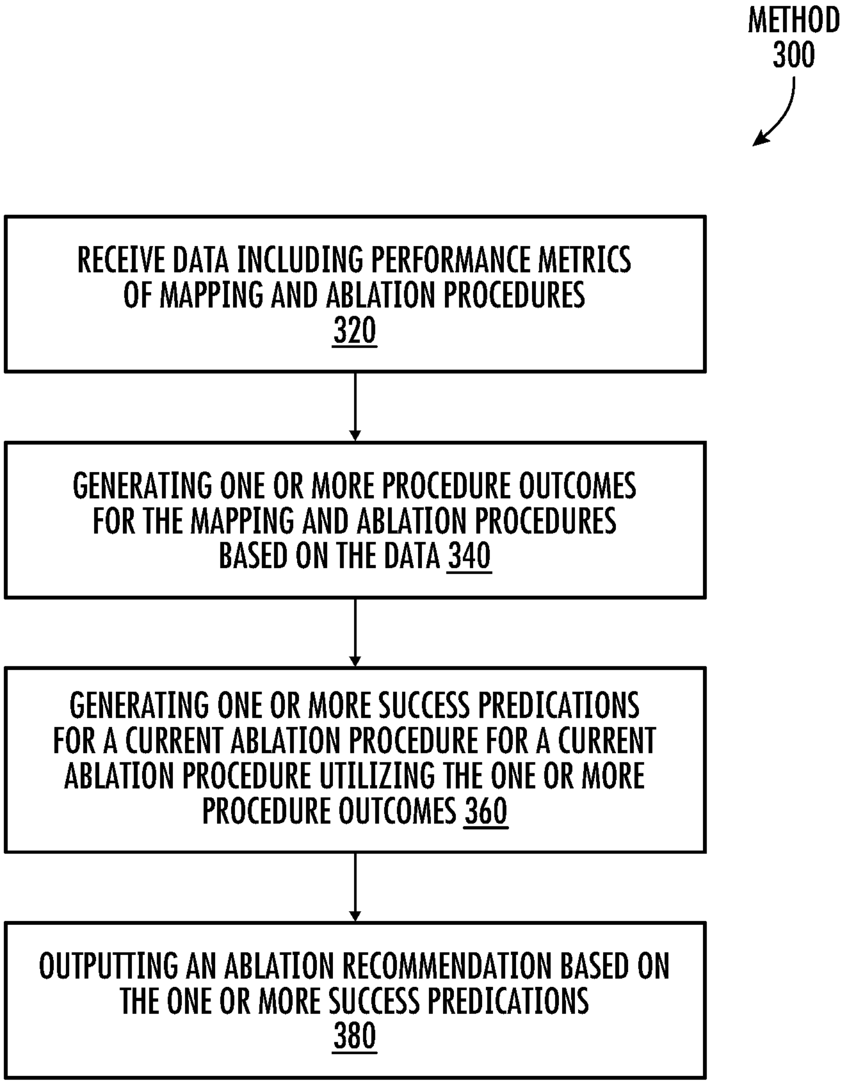
FIG. 3 illustrates a method according to one or more embodiments.

FIG. 3 illustrates a method 300 (e.g., performed by the optimization engine 101 of FIG. 1 and/or of FIG. 2) is illustrated according to one or more exemplary embodiments. The method 300 identifies ablation gaps and provides success predictions by providing a multi-step manipulation of data that improves cardiac arrhythmias diagnosis and treatments. The method 300 is described with respect to ablation procedures by way of example and ease of explanation.

The method begins at block 320, where the optimization engine 101 receives data including performance metrics of mapping and ablation procedures. The data can be considered an input or a plurality of inputs to the optimization engine 101, which is being executed by one or more processors 161 or 222.

The data/inputs, generally, represent biometric data (as described herein), patient parameters, procedure parameters, and/or performance metrics. For example, the biometric data can include anatomical and electrical measurements, as well as other sensor measurements including temperature and impedance, for example, acquired in a significant portion of an atrium during the mapping and ablation procedures. Further, the patient and/or procedure parameters can be related to the mapping and ablation procedures, such as patient characteristics, tissue characteristics, and other data points in an index procedure, as well as patient demographics, information/data related to prior electrophysiology procedures, and acute/long outcome results of the patient. Generally, patient parameters or patient specific information can include body temperature, irrigation temperature, tissue and surface temperature before ablation, tissue and surface temperature during ablation, and tissue and surface temperature after ablation. Further, patient parameters or patient specific information can also include body surface ECG, patient's prior medical history, patient's demographics, IC ECG, voltage maps, type of equipment used, time and date of the procedure, and the anatomy of the patient's heart. Generally, procedure parameters or procedure specific information can include a catheter stability during an ablation procedure and historical outcomes of other patients. Furthermore, the data/inputs can include performance metrics, which include any information indicating or identifying results during and/or of the mapping and ablation procedures. Utilizing these inputs, the optimization engine 101 initiates the technical effect and benefit of identifying ablation gaps and providing success predictions per situation (e.g., time and location) per patient.

The optimization engine 101 receive one or more previous cases, such as prior or old ablation procedures, stored within the system 100 (e.g., a database therein) or received by the system 100. From theses previous cases, the data/inputs can be derived/acquired via maps with a chain of lesions, anatomic maps, and/or electrical maps thereof. From theses previous cases, the data/inputs can be derived/acquired from sensor data thereof, which was generated by one or more sensors (e.g., from the catheter 110 and/or a body surface electrode). For instance, ablation catheters (e.g., the catheter 110) can be used to create tissue necrosis in cardiac tissue of the heart 120 to correct cardiac arrhythmias. In an example ablation procedure, a lesion is produced in the cardiac tissue of the heart 120 of the patient 125 when the catheter 110 is inserted into the heart 120 to contact the cardiac tissue and electromagnetic RF energy is injected from one or more electrodes 111 into the cardiac tissue to cause ablation and production of a lesion. Coordinates of the lesion and parameters of the electromagnetic RF energy can be included in the data/inputs of the ablation procedure.

At block 340, where the optimization engine 101 generates one or more procedure expected outcomes for the mapping and ablation procedures based on the data. Generally, the one or more procedure expected outcomes identify performances of the mapping and ablation procedures, such as acute success or long-term success at preventing aFib reoccurrence (i.e., acute of long-term failure of the ablation).

To determine/generate the one or more procedure expected outcomes, the optimization engine 101 analyzes the data to build and train a model. The optimization engine 101 may inject the data to a model, such as a gold standard where the users have identified gaps and good ablations, and the model outputs the most prominent parameters that predict gap/good ablation. The optimization engine 101 can build and train the model using a supervised approach, an unsupervised approach, and/or a deep learning solution, as described herein. That is, the optimization engine 101 considers all available data/inputs (as described in block 320) when building and training the model. Building/training can be considered a ML phase of the optimization engine 101. For example, the optimization engine 101 collects 10,000 cases with twelve (12) months follow-up information, where each case is associated to a single class redo/long term success and a backpropagation algorithm (as described herein) minimizes a loss function to train learn all weights in a neural network. Then, the optimization engine 101 utilizes the model to analyze the data/inputs (e.g., whether ablation gaps are present) to determine if the mapping and ablation procedures were successful. The model can analyze successes across one or more scenarios, such as different patient groupings (e.g., based on age, gender, health, etc.) and different procedure groupings (e.g., based on type of procedure).

For example, the optimization engine 101 trains by using the prior or old ablation procedures to learn over time different scenarios. In this regard, the optimization engine 101 generates training datasets (from the prior or old ablation procedures) for different patient/procedure groupings respective to the one or more scenarios. The prior or old ablation procedures include previous ablation treatments, locations, etc., as well as cardiac information from follow-up mapping procedures. A patient/procedure grouping includes cases that are similar do to the similar patient demographics (e.g., patients with the same age of blood pressure) and/or procedure condition alignment (e.g., procedure in a same atrium area), etc. The generated training datasets provide whether ablation gaps occurred and whether redo operations were performed for each patient or procedure grouping, which are incorporated into the optimization engine 101.

According to one or more embodiments, the optimization engine 101 utilizes long outcome results of the patient 125 to train the model (and the system 100) by informing/coaching/telling the model which ECG data and the like (e.g., any biometric data relative to the long outcome results) is likely to be healthy or not. Further, this ECG data and the like can be used to train weight of a neural network using a backpropagation approach (e.g., a backpropagation algorithm as described herein).

Figure 4:
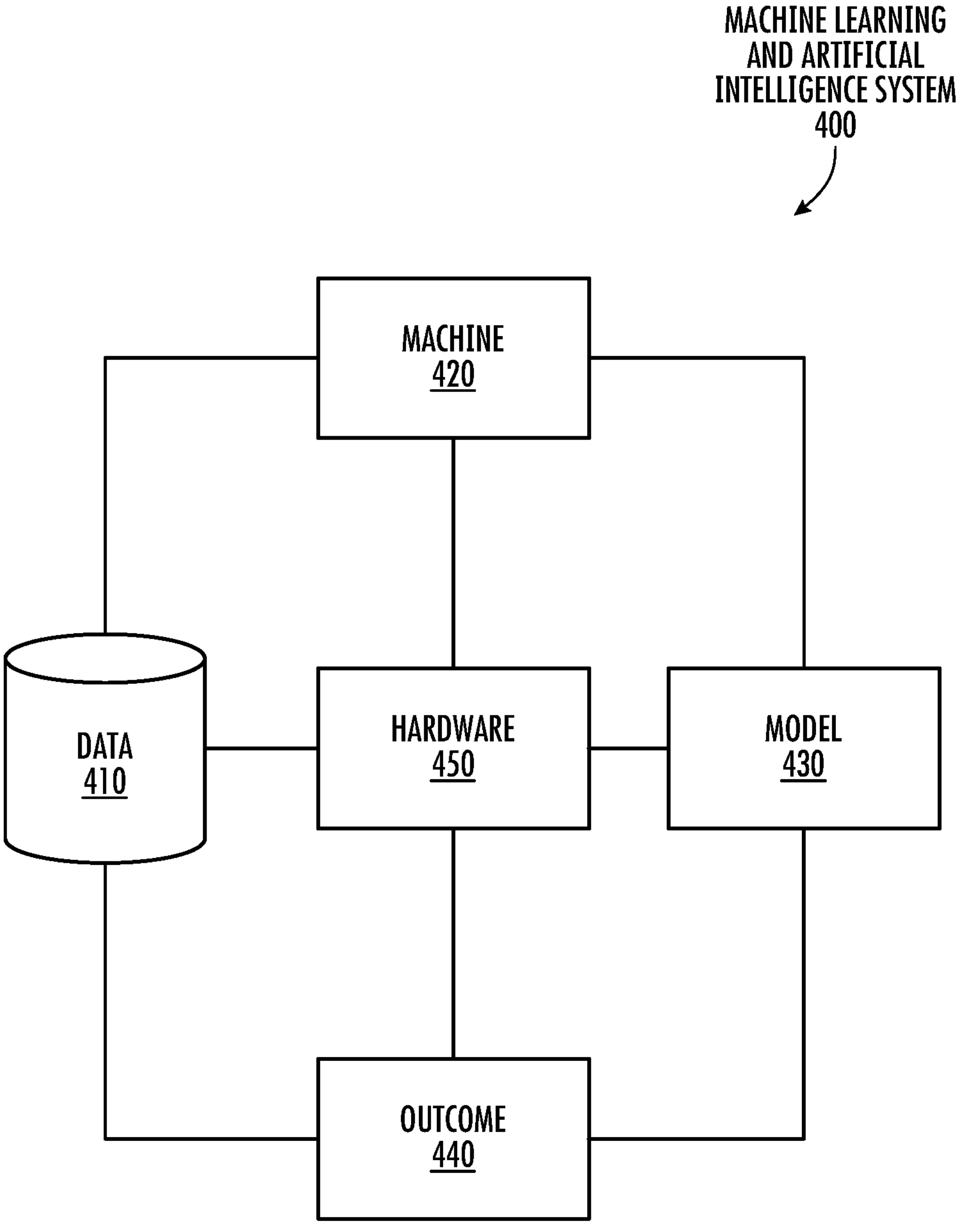
FIG. 4 illustrates a graphical depiction of an AI system according to one or more embodiments.
Figure 5A:
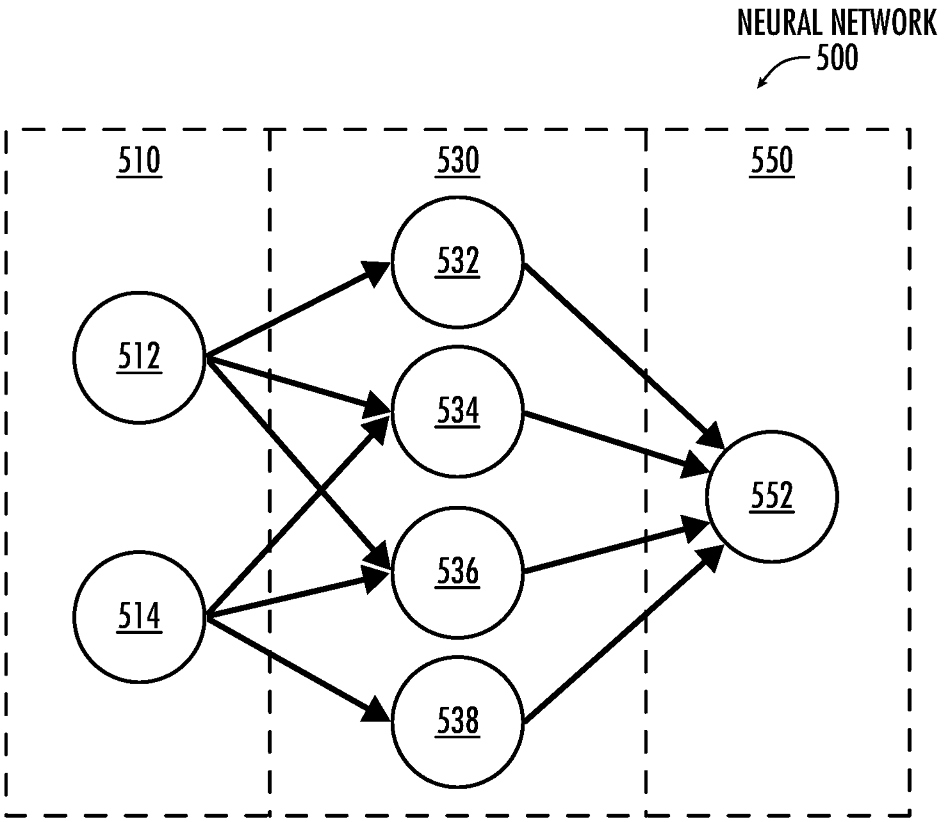
FIG. 5A illustrates an example of a neural network according to one or more embodiments.

For ease of understanding, the building and training of the optimization engine 101 and the model thereof are described with respect to FIGS. 4-5A,B. The descriptions of FIGS. 4-5A,B are made with reference to FIGS. 1-3 where appropriate.

FIG. 4 illustrates a ML/AI system 400 according to one or more embodiments. The ML/AI system 400 includes data 410, a machine 420, a model 430, an outcome 440, and (underlying) hardware 450.

The machine 420, the model 430, and the hardware 450 can represent aspects of the optimization engine 101 of FIGS. 1-2 (e.g., ML/AI algorithm therein), while the hardware 450 can also represent the catheter 110 of FIG. 1, the console 160 of FIG. 1, and/or the apparatus 204 of FIG. 2. In general, the ML/AL algorithms of the ML/AI system 400 (e.g., as implemented by the optimization engine 101 of FIGS. 1-2) operate with respect to the hardware 450, using the data 410, to train the machine 420, build the model 430, and predict the outcomes 440. For instance, the machine 420 operates as the controller or data collection associated with the hardware 450 and/or is associated therewith.

The data 410 can be on-going data or output data associated with the hardware 450. For example, the data 410 can include biometric data of previous cases, such as anatomic data (e.g., anatomical reconstructions, CT, MRI, ultrasound etc.), electrical data (e.g., body surface and IC ECG signals), contact force data, ablation parameters data, tissue touch data, respiration data, fluids data, case specific data, positions, time between original case to redo data, and other determinants The data 410 can also include currently collected data, historical data, or other data from the hardware 450; a case summary by the physician 115; additional imaging data; can include measurements during a surgical procedure (e.g., an ablation procedure) and may be associated with an outcome of the surgical procedure; can include a temperature of the heart 120 of FIG. 1 collected and correlated with an outcome of a heart procedure; and can be related to the hardware 450. According to one or more embodiments, the data 410 can include patient and/or procedure parameters related to the mapping and ablation procedures (e.g., patient characteristics, tissue characteristics, and other data points in an index procedure), patient demographics, information/data related to prior electrophysiology procedures, and acute/long outcome results of the patient 125. The data 410 can be divided by the machine 420 into one or more subsets.

The model 430 is built on the data 410. Building the model 430 can include physical hardware or software modeling, algorithmic modeling, and/or the like that seeks to represent the data 410 (or subsets thereof). In some aspects, building of the model 430 is part of self-training operations by the machine 420. The model 430 can be configured to model the operation of hardware 450 and model the data 410 collected from the hardware 450 to predict the outcome 440 achieved by the hardware 450. Predicting the outcomes 440 can utilize a trained version of the model 430. For example, and to increase understanding of the disclosure, in the case of the heart, if the temperature during the procedure that is between 36.5 degrees Celsius and 37.89 degrees Celsius (i.e., 97.7 degrees Fahrenheit and 100.2 degrees Fahrenheit) produces a positive result from the heart procedure, the outcome 440 can be predicted in a given procedure using these temperatures. Thus, using the outcome 440 that is predicted, the machine 420, the model 430, and the hardware 450 can be built accordingly.

The machine 420 trains the model 430, such as with respect to the hardware 450 and the data 410. This training can also include an analysis and correlation of the data 410 collected. For example, the machine 420 can train the model 430 to determine if a correlation or link exists between the temperature of the heart 120 of FIG. 1 during the heart procedure and the outcome. In accordance with another embodiment, training the machine 420 and the model 430 can include self-training by the optimization engine 101 of FIG. 1 utilizing the one or more subsets. In this regard, the optimization engine 101 of FIG. 1 learns to detect case classifications on a point by point basis.

For the ML/AI system 400 to operate with respect to the hardware 450, analyze the data 410, perform building/training, and predict the outcomes 440, the ML/AI algorithms therein can include neural networks, autoencoders, and backpropagation algorithms. A neural network is a network or circuit of neurons, or in a modern sense, an artificial neural network (ANN), composed of artificial neurons or nodes or cells. An autoencoder is an automatic self-training algorithm. A backpropagation algorithm is used in training feedforward neural networks for supervised learning.

At decision block 360, the optimization engine 101 generates one or more success predictions for a present procedure (e.g., a current ablation procedure). For instance, the optimization engine 101 includes receiving current for a current ablation procedure and executing the generated model to predict a success. Generally, the present procedure or the current ablation procedure can be a present or real-time ablation procedure. Executing can be considered an AI phase of the optimization engine 101. The one or more success predictions can include acute and/or long-term outcomes for the current ablation procedure and redo procedure necessity with respect to one or more ablation gaps. According to one or more embodiments, the optimization engine 101 generates a score at an end of current ablation procedure. The score can be on a range from 0 to 1, with one being the best. Then, based on the score (e.g., the optimization engine 101 outputs 0.8), the physician might search again around the PV, provide additional ablation, and run the optimization engine 101 again. The optimization engine 101 generates a second score (e.g., a score of 0.89) at the end of the second iteration of the current ablation procedure, and the physician 115 decide whether to stop or perform additional ablations, tests, and/or challenges (e.g., adenosine challenge). Thus, the technical effects, advantages, and benefits of the optimization engine 101 include an ability to tell the physician 115 a likelihood that this current ablation procedure can be concluded without a redo, thereby reducing risks to the patient 125 by raising a success probability for this current ablation procedure and/or eliminating unnecessary subsequent procedures.

According to one or more embodiments, the optimization engine 101 utilizes a model and the procedure expected outcomes of the mapping and ablation procedures to analyze biometric data of the current ablation procedure to determine the one or more success predictions. That is, the optimization engine 101 can be utilized during the current ablation procedure to receive inputs that are unique to the patient 125 undergoing the current ablation procedure. Since a model of the optimization engine 101 has been built and trained at block 340, the optimization engine 101 can process the model and these current patient inputs identify ablation gaps and generate new ablation targets (e.g., a potential location for consideration by the physician 115 to prevent acute or long-term failure and a probability of success). The optimization engine 101 can further generate predictions as to the success and/or necessity of these new ablation targets.

Figure 5B:
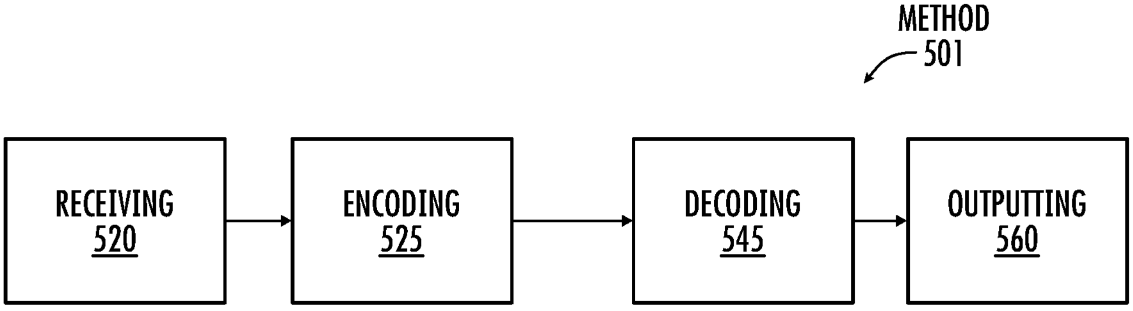
FIG. 5B illustrates a block diagram of a method performed in the neural network according to one or more embodiments.

FIG. 5A illustrates an example of a neural network 500 and FIG. 5B illustrates a block diagram of a method 501 performed in the neural network 500 according to one or more embodiments. The neural network 500 operates to support implementation of the ML/AI algorithms (e.g., as implemented by the optimization engine 101 of FIGS. 1-2) described herein. The neural network 500 can be implemented in hardware, such as the machine 420 and/or the hardware 450 of FIG. 4.

In an example operation, the optimization engine 101 of FIG. 1 includes collecting the data 410 from the hardware 450. In the neural network 500, an input layer 510 is represented by a plurality of inputs (e.g., inputs 512 and 514 of FIG. 5A). With respect to block 520 of the method 501, the input layer 510 receives the inputs 512 and 514. The inputs 512 and 514 can include biometric data. For example, the collecting of the inputs 512 and 514 can be an aggregation of biometric data (e.g., BS ECG data, IC ECG data, and ablation data, along with catheter electrode position data), from one or more procedure recordings of the hardware 450 into a dataset (as represented by the data 410). According to one or more embodiments, the inputs 512 and 514 can include twelve (12) input ECG leads of the system 100.

According to one or more embodiments, with respect feature extraction for a training set, the inputs 512 and 514 can include BS ECG before a first procedure, twelve (12) lead BS ECG post procedure (e.g., if in NSR), categorical/numerical information on patient (e.g., gender, left atrium volume, age, body mass index, as described herein, and outcomes (e.g., acute and/or long), such as categorical/numerical information indicated from ECG recordings or real ECG signals from link or other means.

At block 525 of the method 501, the neural network 500 encodes the inputs 512 and 514 utilizing any portion of the data 410 and the one or more procedure expected outcomes produced by the ML/AI system 400 to produce a latent representation or data coding. The latent representation includes one or more intermediary data representations derived from the plurality of inputs. According to one or more embodiments, the latent representation is generated by an element-wise activation function (e.g., a sigmoid function or a rectified linear unit) of the optimization engine 101 of FIG. 1. As shown in FIG. 5A, the inputs 512 and 514 are provided to a hidden layer 530 depicted as including nodes 532, 534, 536, and 538. The neural network 500 performs the processing via the hidden layer 530 of the nodes 532, 534, 536, and 538 to exhibit complex global behavior, determined by the connections between the processing elements and element parameters. Thus, the transition between layers 510 and 530 can be considered an encoder stage that takes the inputs 512 and 514 and transfers it to a deep neural network (within layer 530) to learn some smaller representation of the input (e.g., a resulting the latent representation).

The deep neural network can be a CNN, a long short-term memory neural network, a fully connected neural network, or combination thereof. This encoding provides a dimensionality reduction of the inputs 512 and 514. Dimensionality reduction is a process of reducing the number of random variables (of the inputs 512 and 514) under consideration by obtaining a set of principal variables. For instance, dimensionality reduction can be a feature extraction that transforms data (e.g., the inputs 512 and 514) from a high-dimensional space (e.g., more than 10 dimensions) to a lower-dimensional space (e.g., 2-3 dimensions). The technical effects and benefits of dimensionality reduction include reducing time and storage space requirements for inputs 512 and 514, improving visualization of inputs 512 and 514, and improving parameter interpretation for machine learning. This data transformation can be linear or nonlinear. The operations of receiving (block 520) and encoding (block 525) can be considered a data preparation portion of the multi-step data manipulation by the optimization engine 101.

At block 545 of the method 510, the neural network 500 decodes the latent representation. The decoding stage takes the encoder output (e.g., the resulting the latent representation) and attempts to reconstruct some form of the inputs 512 and 514 using another deep neural network. In this regard, the nodes 532, 534, 536, and 538 are combined to produce in the output layer 550 an output 552, as shown in block 560 of the method 510. That is, the output layer 590 reconstructs the inputs 512 and 514 on a reduced dimension but without the signal interferences, signal artifacts, and signal noise. Examples of the output 552 include cleaned biometric data (e.g., clean/denoised version of IC ECG data or the like). According to one or more embodiments, with respect to a deep learning solution of the optimization engine 101, a CNN autoencoder for twelve (12) lead BS ECG is utilized as the neural network 500. The CNN autoencoder can be a deep CNN that is pre-trained or trained as described herein. Thus, according to one or more embodiments, the output 552 includes reconstructed ECG from the data provided by the twelve (12) lead BS ECG. The technical effects and benefits of the cleaned biometric data include enabling more accurate monitor, diagnosis, and treatment any number of various diseases.

At block 380, the optimization engine outputs an ablation recommendation based on the one or more success predictions. According to one or more embodiment, the optimization engine 101 provides on the display 165 one or more user interfaces that illustrate a mapping of the current ablation procedure, as well as the ablation recommendation. The ablation recommendation an include an area for ablation based on the one or more success prediction and a probability for a redo procedure. In this way, the optimization engine 1010 provides to the physician 115 whether a redo of any procedure is likely to have a positive outcome and provide such determinations with a correct/suggested course of action. Thus, the technical effects, advantages, and benefits of the optimization engine include reducing risks to the patient by raising a success probability for a next procedure and/or eliminating unnecessary subsequent procedures.

Figure 6:
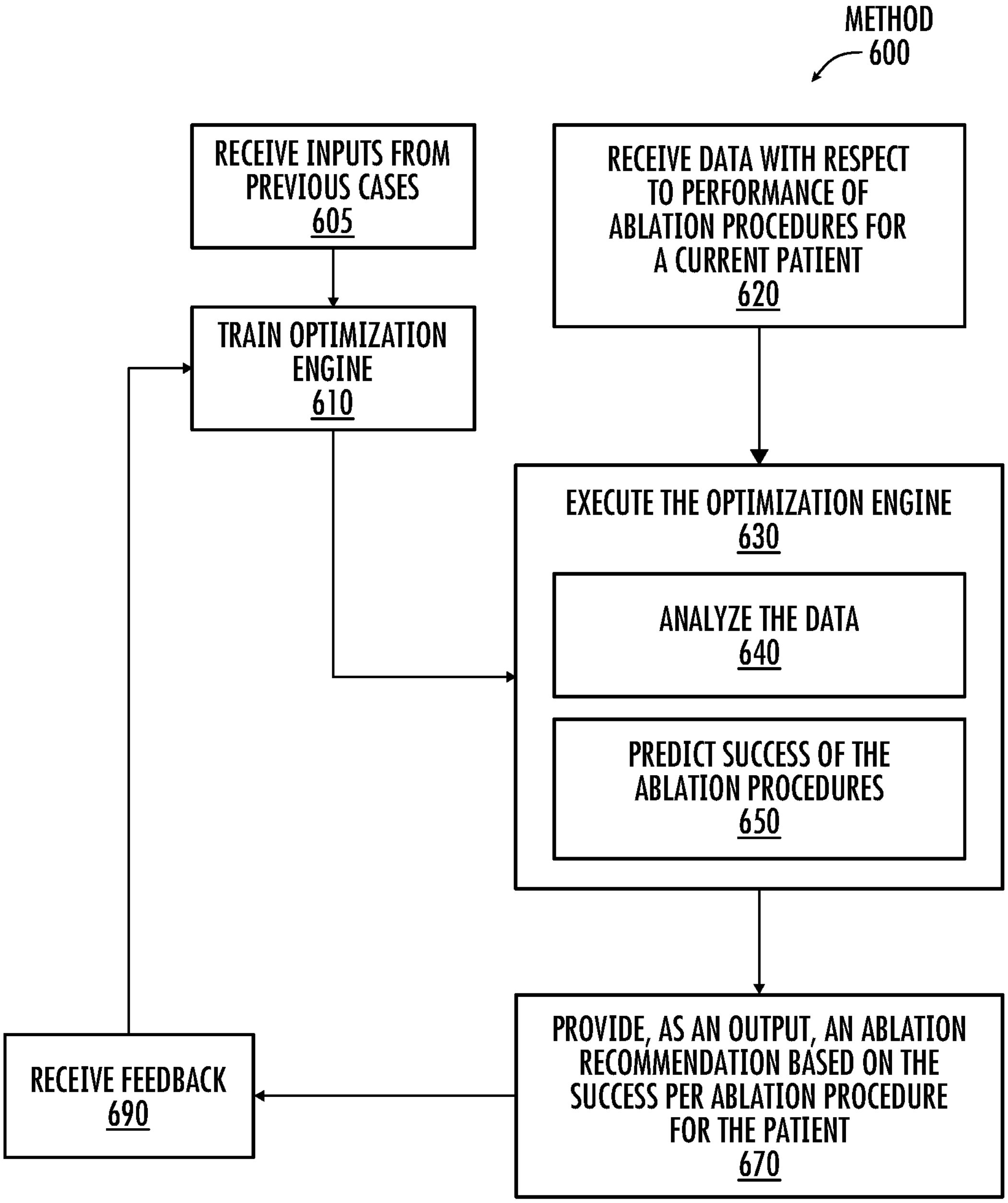
FIG. 6 illustrates a method according to one or more embodiments.

FIG. 6 illustrates a method 600 according to one or more exemplary embodiments. The method 600 (e.g., performed by the optimization engine 101 of FIG. 1 and/or of FIG. 2) is illustrated according to one or more exemplary embodiments. The method 600 is described with respect to ablation procedures by way of example and ease of explanation. The method 600 identifies ablation gaps and provides success predictions through a multi-step manipulation of data that improves cardiac arrhythmias diagnosis and treatments.

Generally, success rates for atrial arrhythmia treatments via catheter ablations are not always completely successful. For example, some portion of patients (e.g., 5-40%) experience an atrial arrhythmia with a one year follow up. These patients may suffer from re-connections in the ablation chain, which require repeat ablation in a location that was ablated in the past, or might suffer a disease relapse stemming in a driver that was not targeted for ablation in a first procedure. The method 600 seeks to avoid unnecessary subsequent procedures, while identifying ablation gaps and recommendations to increase a success probability of necessary subsequent procedures.

The method 600 begins at block 605, where the optimization engine 101 receives inputs from previous cases (e.g., previous mapping and ablation procedures). In a practical example, the optimization engine 101 analyzes the previous cases, with and without redo procedures, to derive, as the inputs, the data 410 and the performance metrics.

According to one or more embodiments, in the treatment of atrial or ventricular arrhythmias, the optimization engine 101 places ablation applications next to each other in a contiguous manner to create a contiguous ablation line, where a gap in the line due to a lesion being not deep enough or not close enough to each other creates a breach of electricity through the ablation chain, deeming the ablation chain ineffective. These areas of breach are very hard to find and identify manually, which leads to longer procedures with lower success rates.

According to one or more embodiments, the data 410 and the performance metrics can be acquired via a map with a chain of lesions, an anatomic map or anatomical reconstruction with the information of wall depth, and/or an electrical map. To support predictions of the method 600, the optimization engine 101 may utilize data from previous ablations, such as ablation sites, ablation index, anatomical maps, from both the initial ablation study and any redo procedures. The data 410 and the performance metrics can also be derived gathered using backup studies. This data 410 and the performance metrics can be compared before the redo to the redo locations. In some embodiments, the data 410 and the performance metrics (e.g., for training) may be acquired from a magnetic field around the patient 125 from the magnetic sensors that are included in the catheter 110. The data 410 and the performance metrics may also be obtained using the ACL feature, the electrode sensors using the signal filters algorithms, the Mesh/Images, registration algorithm, and ablation index parameters and algorithms.

At block 610, the optimization engine 101 trains. In this regard, the optimization engine 101 creates/builds a model that can be used in real time procedures to identify potential areas where the physician 115 should take a second look and revalidate those areas to avoid procedure failure, procedure prolongation, or a redo procedure.

According to one or more embodiments, the acquired data 410 and the performance metrics (e.g., original case data, IC ECG and positions, additional imaging data, and a case summary by the physician 115) can be inputted into a non-supervised algorithm, deep learning algorithm, autoencoder, and/or backpropagation algorithm for analysis by the optimization engine 101. The data 410 and the performance metrics can be pre-processed to extract relevant features for the task of predicting redo success rate both for the specific patient and subgroups similar to the patient, and evaluating patient risk of requiring a redo procedure. The optimization engine 101 can analyze the data for potential missing ablation steps to try to determine if the ablation will require a redo. That is, by having the data 410 and the performance metrics as to outcomes, and what procedures required a redo procedure, and where the ablation were placed to treat the patient in the redo procedure, the optimization engine 101 can learn whether or not a specific ablation procedure will require a redo.

Figure 7:
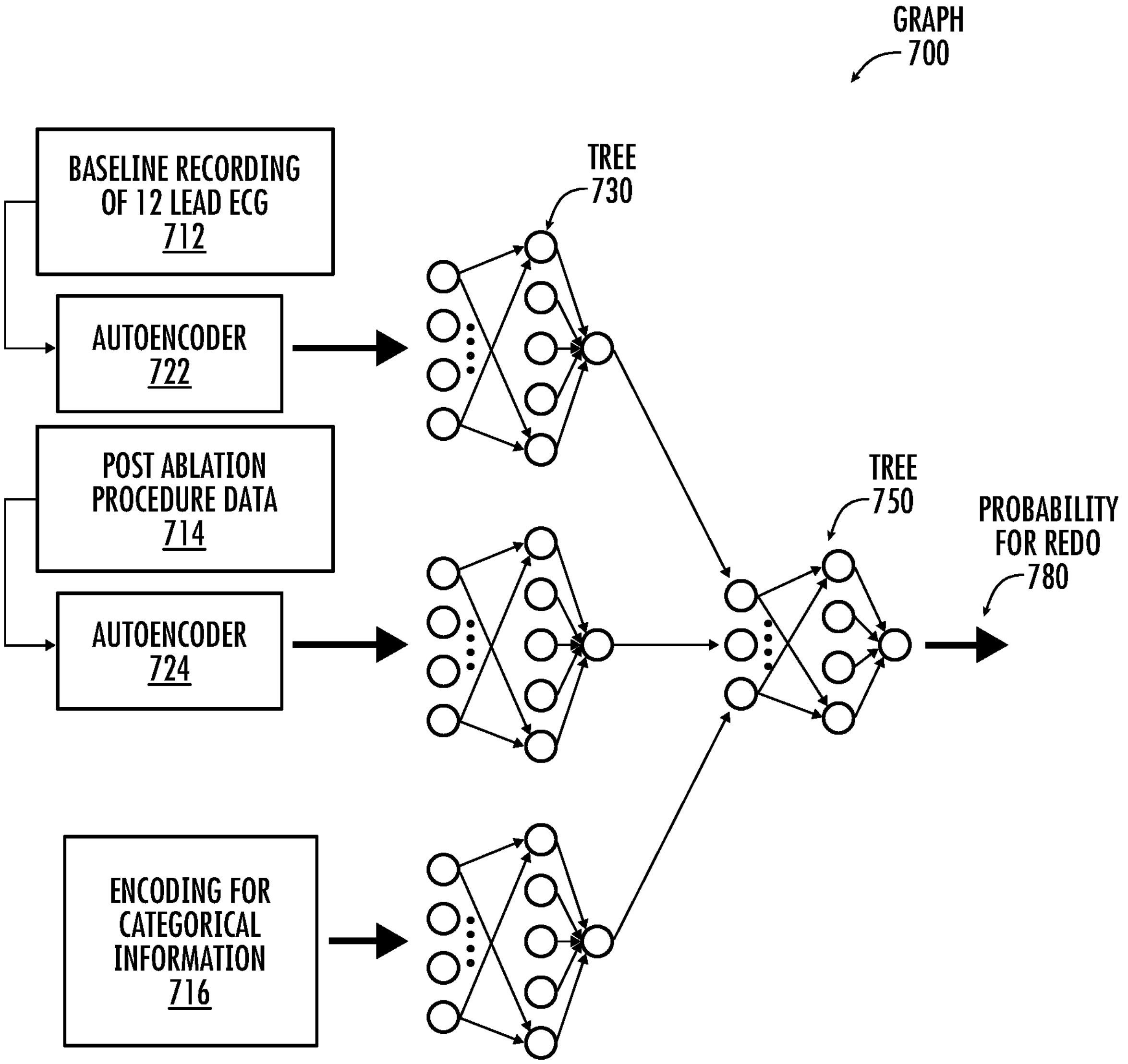
FIG. 7 illustrates a graph according to one or more embodiments.

FIG. 7 illustrates a graph 700 that includes one or more aspect of the ML/AI algorithm of the optimization engine 100. As shown, data 712, 714, and 716 can be inputted into one or more autoencoders 722 and 724 and trees 730 and 750, which represent one or more ML/AI algorithms, to output a probability for redo 780. According to one or more embodiments, additional inputs can include outcomes (e.g., acute and/or long), such as categorical/numerical information indicated from ECG recordings or real ECG signals from link or other means.

The data 712 can include baseline recordings of twelve (12) lead ECG and/or signals from stationary catheter, such as a coronary sinus (CS) catheter. The data 714 can include post ablation procedure data. According to one or more embodiments, the data 712 and the data 714 are fed through pre-trained CNN autoencoders (e.g., autoencoders 714 and 716 to provide training dataset).

At block 620, the optimization engine 101 receives data with respect to performance of ablation procedures for a current patient (e.g., the patient 125). The optimization engine 101 present data as described below with respect to a performance of a current ablation procedure. For instance, during PV isolation procedures, anatomical and electrical data are acquired in a significant portion of an atrium. This information can provide an indication to estimate if additional ablation steps will be required based on the model and optimization engine 101 analyses of block 630.

At block 630, the optimization engine 101 executes. For instance, the optimization engine 101 compares present data with the model to predict a success, whether acute or long term, for a current ablation procedure. Block 630 can include sub-block 640 and 650. At sub-block 640, the optimization engine 101 analyzes the data to determine ablation gaps. At sub-block 650, the optimization engine 650 utilizes the ablation gaps to predict success of the ablation procedures.

According to one or more embodiments, the optimization engine 101 analyzes the present data with respect to the data 410, the performance metrics, and the model to determine potential ablation gaps. Returning to FIG. 7, the data 716 can be present data that includes categorical information, such as gender, weight, body mass index (BMI), atrium volume, left atrium volume, CHADS or CHADS2 (i.e., a score used to determine treatment for atrial-fibrillation patients in danger of stroke), etc. In this way, the data 712, 714, and 716 are analyzed together through the trees 730 and 750. The tree 730 can be fully connected neural network with ten (10) hidden layers, such the pre- and post-ablation procedure data 712 and 714 and the categorical data 716 are fed thereto. An output of the trees 730 can then be fed to the tree 750 with a single hidden layer with single neuron at an output for the probability for redo 780.

Once the present data is analyzed, the optimization engine 101 utilizes the determination of the potential ablation gaps and the model to predict the acute and long-term success of an ablation procedure. For instance, predicting whether or not a redo procedure may be necessary can be obtained by learning parameters of the current patient 125 (e.g., learning patient and tissue characteristics through an index procedure) comparing the procedure cases of like patients, such as via non-supervised algorithm, deep learning algorithm, autoencoder, and/or backpropagation algorithm of the optimization engine. In addition to the patient and tissue characteristics, the optimization engine 101 can learn additional ablations added to close acute reconnections, data points of respective redo procedures performed, and locations ablated to terminate the arrhythmia in the redo procedures, well as other data points. Once learned, the optimization engine 101 can predict which are the locations potentially responsible for acute or long-term failure. The optimization engine 101 can recommend to address any failures in the redo procedure and/or place a special emphasis on any failures in the current ablation procedure. In this regard, the optimization engine 101 can identify areas for ablation outside of the veins or areas prone for reconnection. The optimization engine 101 can be adapted for arrhythmias other than aFib. Analyzing data from redo procedures can contribute to understand real time ablation whether a gap can be formed later on (e.g., tissue recovery) and indication can be visualized to the physician 115 on that location.

At block 670, the optimization engine 101 provides outputs. The outputs can be provided via the one or more user interfaces, described herein, on the display 165 or the like. The outputs can include one or more ablation recommendations based on the success per ablation procedure of the patient 125. For instance, the optimization engine 101 outputs to the physician 115 a potential location for potentially needed ablation based upon the prediction to avoid electrical reconnections in the ablation chain. The optimization engine 101 can also output additional potential locations to ablate in order to avoid electrical reconnections.

According to one or more embodiments, the optimization engine 101 provides as an output to the physician 115 the likelihood of a needed redo procedure based on the prediction. Returning to FIG. 7, the probability for redo 780 can be a percentage, a score, a value represented on a scale (e.g., from 0 to 1, with 0 being the lowest probability for redo). According to one or more embodiments, the optimization engine 101 can conclude based on a results of an ablation set (e.g., a training dataset) a likelihood of redo for this patient. As described herein, an example training dataset can include recordings of patients undergoing first ablation treatments, as well as optional clinical categorical patient information, and/or a status of aFib free from follow-up mapping procedures. That is, the optimization engine 101 provides an indication 115 to the physician whether the current ablation is good enough based on previous cases or whether the current ablation might have potential gaps that will result with a redo, and suggests where those might be on the patient's cardiac 3D map.

At block 690, the optimization engine 101 receives feedback. Generally, feedback can include any information provided directly by the physician 115 before, during, or after a current ablation procedure to the optimization engine 101. The feedback can be provided via the one or more user interfaces, described herein, on the display 165 or the like. According to one or more embodiments, when the physician 115 commences an ablation procedure, there is information gained before and during the procedure that can be utilized to determine whether or not a redo procedure is likely to be necessary. This information can be utilized to further train the model and the optimization engine 101. This information can also be analyzed, in real time, using ML/AI of the optimization engine 101 to indicate to the physician 115 during the current ablation procedure if additional ablations or a redo procedures may be required or likely to occur. That is, because it is desired to prevent redoes based on previous study cases, any real-time indication can help the physician 115 concentrate on specific areas, to check and validate these areas to see that the ablation is sufficient.

According to one or more embodiments, the optimization engine 101 can track the procedure workflow (e.g., for example in atrial fibrillation), identify the anatomy reconstruction and mapping phases, the catheter 110 insertion into the pulmonary veins, the ablation phase, waiting time for validations, repeated ablation in the location and so forth, and learn this workflow and process patterns. In an embodiment specific for aFib, the optimization engine 101 can identify the insertion of the catheter 110 into the pulmonary veins for purposes of validation of isolation and identify whether active signals are measured on the catheter 110.

If active signals are measured, the optimization engine 101 can identify and suggest the earliest activation on the Dx catheter likely correlated with the electrical breach. The optimization engine 101 can then mark on the CARTO® system the areas that are most likely to be the cause for the breach (e.g., marked with an arrow, via coloring on the map according to the area's likelihood to cause the breach or in any other way, or any other potential presentation). Thus, through ML/AI, the optimization engine 101 enables an identification of the workflow stages, the phase in which the operator is looking to validate the ablation acute success, and/or the ability to link between the earliest signal on the catheter 110 and a specific location on the anatomical structure.

Additionally, during a triangulation process, any acquired data can indicate where an origin of an arrhythmia is probable to be, and which points are the most informative to validate and discover the origin in the most efficient data. The optimization engine 101 learns from previous maps, anatomical structure and mapping sequence to recommend the best course of action at each point.

Accordingly, during an ablation procedure, any acquired data can be utilized by the optimization engine 101 to present to the physician 115 an area for ablation where the physician 115 may have more success and lesser chance of requiring a redo procedure. For example, the optimization engine 101 may read the position of the catheter 110 in the heart 120 from the moment the catheter 110 is inserted into a vein and generate, on a screen, the locations for recommended ablation based upon the ML algorithm performed and prediction of the outcomes. Thus, the optimization engine 101 learns from the ablation gaps from previous cases, as well as current data to project locations for the physician 115 where to perform an ablation during a current procedure that will have less need for a redo procedure.

With reference to the ML/AI algorithms described herein, neural networks, autoencoders, and backpropagation algorithms are now described.

An ANN involves a network of processing elements (artificial neurons) which can exhibit complex global behavior, determined by the connections between the processing elements and element parameters. These connections of the network or circuit of neurons are modeled as weights. A positive weight reflects an excitatory connection, while negative values mean inhibitory connections. Inputs are modified by a weight and summed using a linear combination. An activation function may control the amplitude of the output. For example, an acceptable range of output is usually between 0 and 1, or it could be −1 and 1. In most cases, the ANN is an adaptive system that changes its structure based on external or internal information that flows through the network.

In more practical terms, neural networks are non-linear statistical data modeling or decision-making tools that can be used to model complex relationships between inputs and outputs or to find patterns in data. Thus, ANNs may be used for predictive modeling and adaptive control applications, while being trained via a dataset. The self-learning resulting from experience can occur within ANNs, which can derive conclusions from a complex and seemingly unrelated set of information. The utility of artificial neural network models lies in the fact that they can be used to infer a function from observations and also to use it. Unsupervised neural networks can also be used to learn representations of the input that capture the salient characteristics of the input distribution, and more recently, deep learning algorithms, which can implicitly learn the distribution function of the observed data. Learning in neural networks is particularly useful in applications where the complexity of the data (e.g., the biometric data) or task (e.g., monitoring, diagnosing, and treating any number of various diseases) makes the design of such functions by hand impractical.

Neural networks can be used in different fields. Thus, the ML/AI algorithms therein can include neural networks that are divided generally according to tasks to which they are applied. These divisions tend to fall within the following categories: regression analysis (e.g., function approximation) including time series prediction and modeling; classification including pattern and sequence recognition; novelty detection and sequential decision making; data processing including filtering; clustering; blind signal separation, and compression. For example, Application areas of ANNs include nonlinear system identification and control (vehicle control, process control), game-playing and decision making (backgammon, chess, racing), pattern recognition (radar systems, face identification, object recognition), sequence recognition (gesture, speech, handwritten text recognition), medical diagnosis and treatment, financial applications, data mining (or knowledge discovery in databases, "KDD"), visualization and e-mail spam filtering. For example, it is possible to create a semantic profile of patient biometric data emerging from medical procedures.

According to one or more embodiments, the neural network can implement a long short-term memory neural network architecture, a convolutional neural network (CNN) architecture, or other the like. The neural network can be configurable with respect to a number of layers, a number of connections (e.g., encoder/decoder connections), a regularization technique (e.g., dropout); and an optimization feature.

The long short-term memory neural network architecture includes feedback connections and can process single data points (e.g., such as images), along with entire sequences of data (e.g., such as speech or video). A unit of the long short-term memory neural network architecture can be composed of a cell, an input gate, an output gate, and a forget gate, where the cell remembers values over arbitrary time intervals and the gates regulate a flow of information into and out of the cell.

The CNN architecture is a shared-weight architecture with translation invariance characteristics where each neuron in one layer is connected to all neurons in the next layer. The regularization technique of the CNN architecture can take advantage of the hierarchical pattern in data and assemble more complex patterns using smaller and simpler patterns. If the neural network implements the CNN architecture, other configurable aspects of the architecture can include a number of filters at each stage, kernel size, a number of kernels per layer.

An autoencoder is an automatic self-training algorithm. In some cases, autoencoders include a training algorithm that implements a deep learning training loss function and, more specifically, an autoencoder clinical weighted MSE loss function. Further, autoencoders can execute in one or more modes. For instance, a first mode can include building a dedicated graphic user interface comprising one or more filters. The dedicated GUI provides an ability to filter out noise component manually based on set of predefined filters (raw data signals are usually recorded with noise). In this way, the autoencoder experiences at least two sets of signals, such as an original signal that contains noise and a denoised signal that is used to train the autoencoder. A second mode can include recording noise in a control environment and adding the noise to the clean signal data (e.g., a clean version from previous stage). The noise can include least one of power line noise, contact noise, deflection noise, Fluro noise, and ventricular far field.

An autoencoder can reconstruct an input from a corrupted version of itself by forcing a hidden layer to discover more robust features and prevents relearning a particularly identity. In this regard, the autoencoder forces a hidden layer therein to discover more robust features (i.e., useful features that will constitute better higher-level representations of the input) and prevent it from learning a particularly identity (i.e., always returning to a same value). Further, the autoencoder encodes the input (e.g., to preserve information about the input) and reverses the effect of a corruption process stochastically applied to the input of an autoencoder.

For example, the autoencoder clinical weighted MSE loss function is a multi-step data manipulation of electrical signals to detect or quantify or detect high frequency zones in a signal and then use autoencoder clinical weighted MSE loss function to enhance a signal reconstruction around atrium activity.

A backpropagation algorithm is used, in deep learning, in training feedforward neural networks for supervised learning. The adjective "deep" in deep learning comes from the use of multiple layers in the network. Backpropagation algorithms work by computing a gradient of a loss function with respect to each weight by the chain rule. The weights are updated to minimize a loss function. Further, gradient descent or variants, such as a stochastic gradient descent, can be used.

Figure 8:
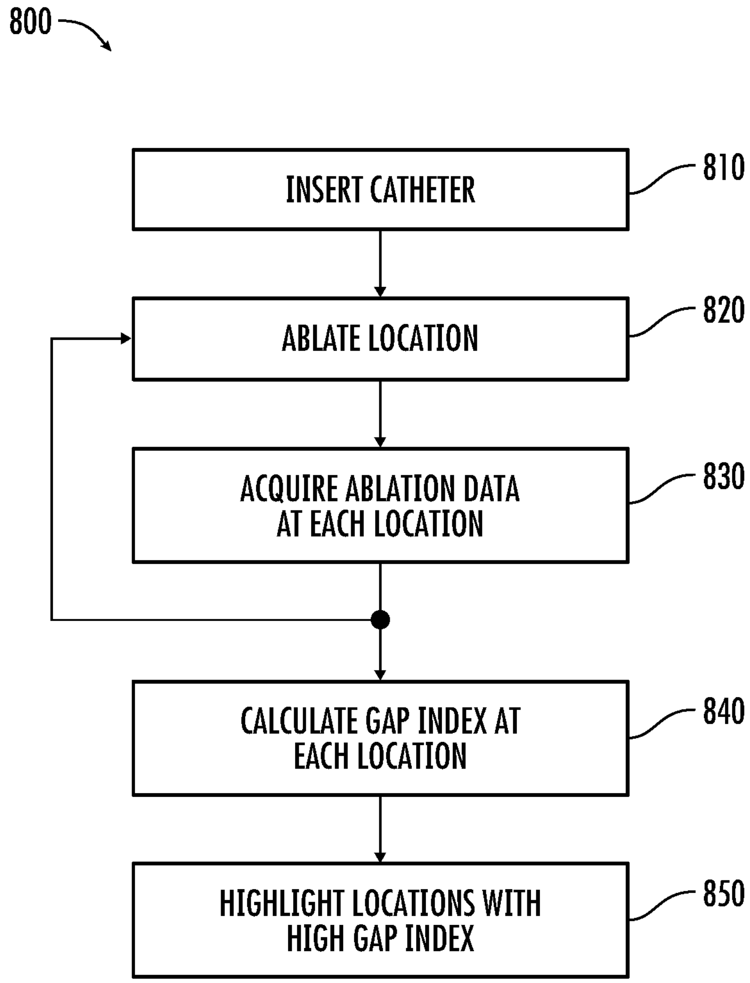
FIG. 8 illustrates a method of a gap finder according to an embodiment.

FIG. 8 illustrates a method 800 of a gap finder according to an embodiment. The parameters of each ablation site, that are acquired during the ablation procedure, may be used to generate a Gap Index (GI) for the site. A high GI indicates a high probability of a gap. The site parameters are Ablation Index (AI), Average Temperature (T), Quality of Stability (QS), and Distance to Nearest Stable site (DS).

Ablation Index (AI) may be derived from Force, Power, and Time of ablation of the site. The AI is defined in Eq. 1:

$$\text{Depth}(t) = \left(v2 \times \int_0^T CF(t)^{v3} \times P(t)^{v4}\, dt\right)^{v1}, \qquad \text{Eq. 1}$$

QS may be derived from the site stability algorithm. Site stability algorithm as explained in greater detail in U.S. patent application Ser. No. 17/188,844, "PROBE-CAVITY MOTION MODELING", filed Mar. 1, 2021, for Meir Bar-Tal, Erez Silberschein, Liron Shmuel Mizrahi, Alona Sigal, and Aharon Turgeman which is incorporated by reference herein. The DS may be determined using the site stability algorithm. The stability quality index is a function of mean distance of the catheter from the center of mass of the site. Very stable ablation may provide low stability index value, less stable ablation may provide high stability index value.

The Gap Index for an ablation site is given by Eq. 2:

$$GI=f(AI,T,QS,DS) \qquad \text{Eq. 2}$$

where f( ) is a function of the parameters listed above. ML may be used to determine probability of a Gap and/or to determine a relationship between the above parameters and the probability of a gap.

As illustrated in FIG. 8, the method includes after an ablation catheter is inserted at 810 into a desired region, the ablation catheter is used to ablate a number of locations at 820 at the region. Once all or the desired locations have been ablated, data for the ablations are collected at each location at 830, and a processor calculates the GI for each location at 840. The processor highlights at 850 on a map or depiction of the ablation locations with a high GI, i.e., those sites having a high probability of being a gap. Showing high probability gap locations to the physician reduces the time required by the physician to search for gaps.

As would be understood, the relationships between the various site parameters may be important. Specifically, a relationship may exist in and among the various parameters of AI, T, QS, and DS. The present system and method is directed to using parameters to verify or validate other parameters to insure quality ablation and calculation in the GI. Detail on the combinations of parameters that are important and how these deductions are made is presented below. For example, the set of parameters (location, contact force, temperature, impedance) may need to all be met in order to view the ablation as successful. In the examples of FIG. 10-14 below, the various combinations of these four parameters are lacking, and this leads to poor or suspect ablations as described.

Figure 9:
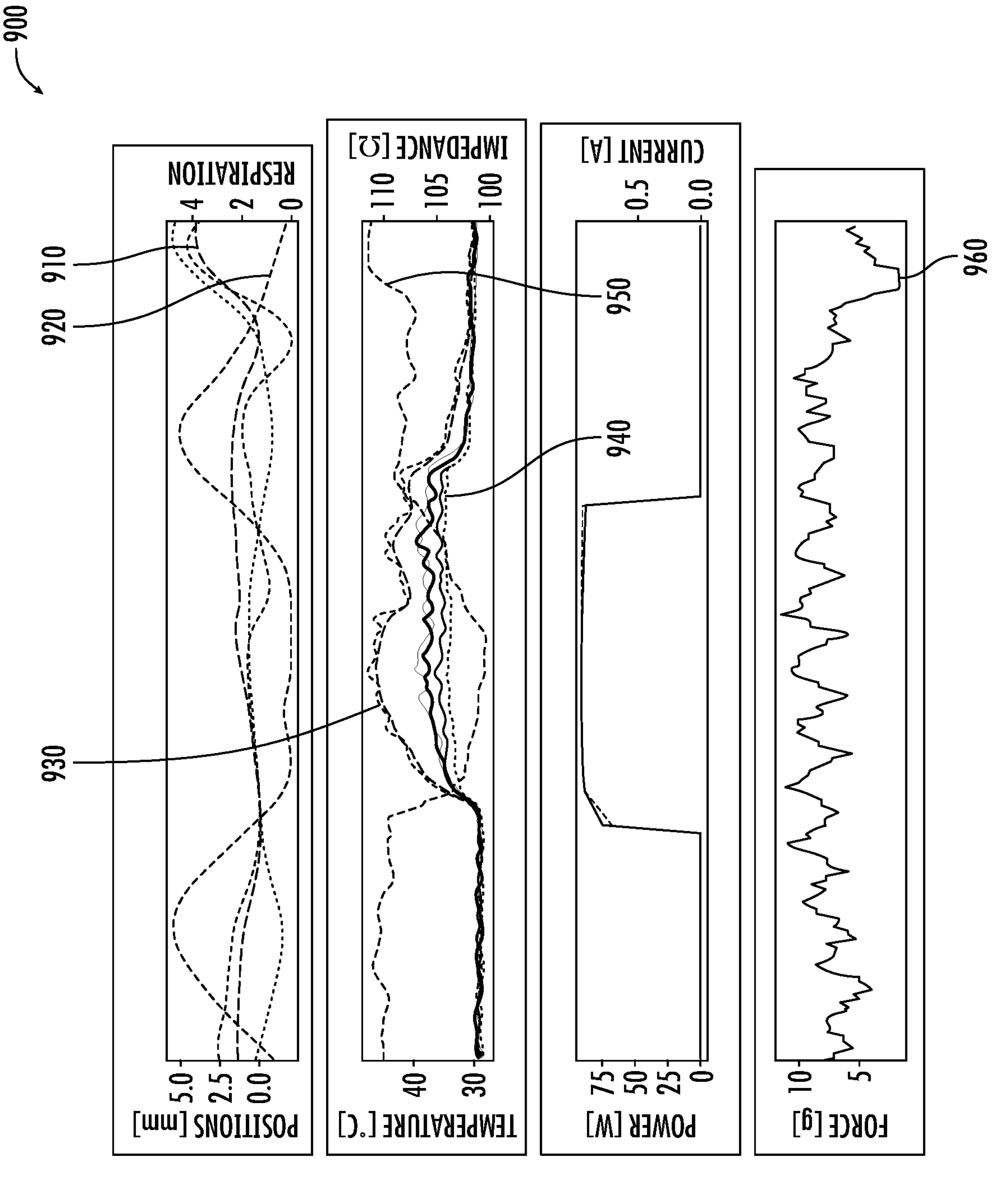
FIGS. 9-14 provide plots associated with parameters to demonstrate the importance and relationships associated with the parameters.

FIGS. 9-14 provide graphs of data associated with the parameters described above to demonstrate the importance and relationships associated with the parameters. FIG. 9 generally provides a framework of description of the data and provides the framework for the analysis that will be provided in the other FIGS. 10-14.

Specifically, FIG. 9 illustrates a set of general graphs 900. In the first graph of set, the left axis plots the positions of the XYZ location 910 as seen in the CARTO system. The data may include filtering such as heart-beat filtering, for example. The right axis of the first graph of the set represents the respiration signal with reference to plot 920.

As illustrated in the second graph, the left axis includes the temperature with reference to the plot of maximum temperature 930 and with reference to the plot of the six temperatures of QDOT 940. The right axis of the second graph provides a scale for impedance with reference to the plot of the impedance 950.

As illustrated in the third graph of the set scale is provided for power on the left and a scale for current on the right. As illustrated the current a power track with only slight deviations.

As illustrated in the fourth plot of the set, there is a scale for force on the left side with reference to a plot of the force 960.

Generally, as provided in FIG. 9, the parameters described above are included in the graphs of data to demonstrate the importance and relationships associated with the parameters.

Figure 10:
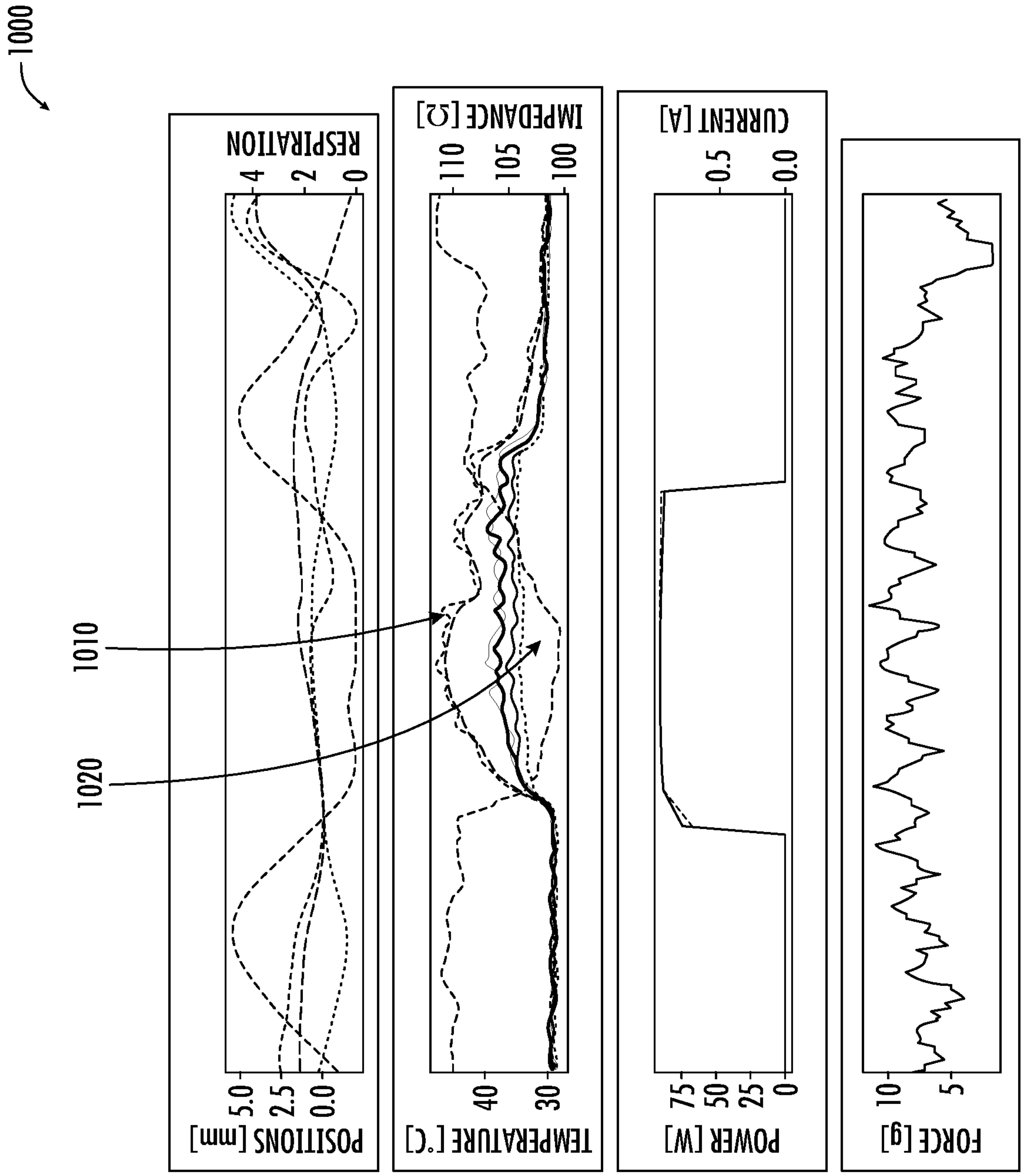

FIG. 10 illustrates a set of graphs 1000 of parameters during an ablation procedure as described above with respect to FIG. 9. Set of graphs 1000 illustrates a configuration where the location is stable and contact force is stable. Specifically, with respect to the location, the first graph of the set provides the curves of the positions indicating a small variation during the plot of a few millimeters. With respect to the contact force, the fourth plot of the set indicates that the contact force varies slightly across a scale of a few grams. The third plot of the set illustrates the power and current generally in line with that provided in FIG. 9. With respect to the second portion of the sets of graphs, there is illustrated a temperature drop and an impedance rise. The temperature drops 1010 more than approximately 5° C. over a short time and impedance rises 1020 at the same time by more than approximately 5 Ω. This combination of temperature drop and impedance rise may indicate that the catheter is not heating the same spot on the tissue.

Figure 11:
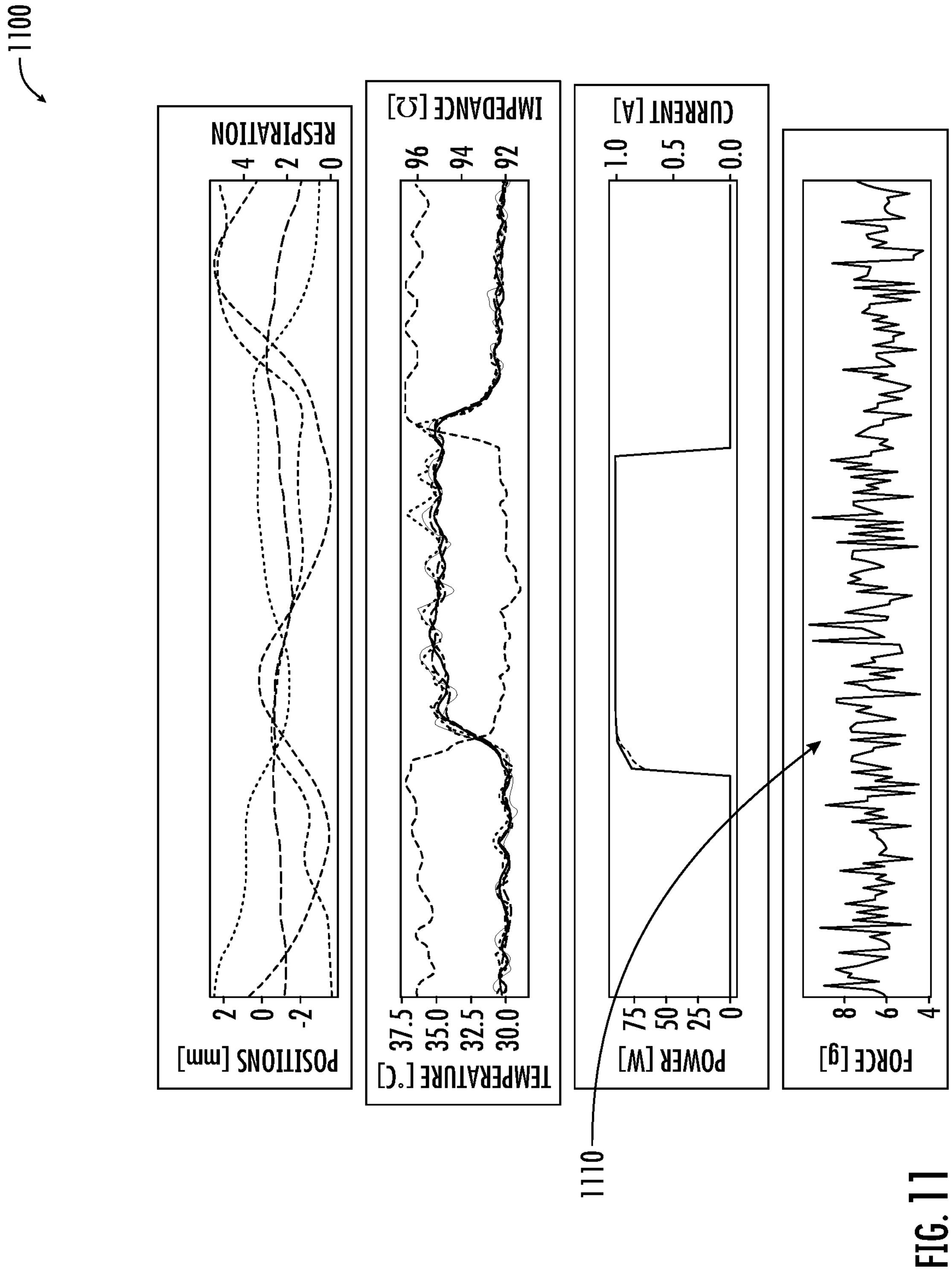

FIG. 11 illustrates a set of graphs 1100 of the parameters of FIG. 9. Set of graphs 1100 illustrates a stable location. Specifically, with respect to the location, the first graph of the set provides the curves of the positions indicating a small variation during the plot of a few millimeters. Set of graphs 1100 indicates a low applied contact force 1110 applied to the tissue leading to a low temperature rise and related impedance drop.

Figure 12:
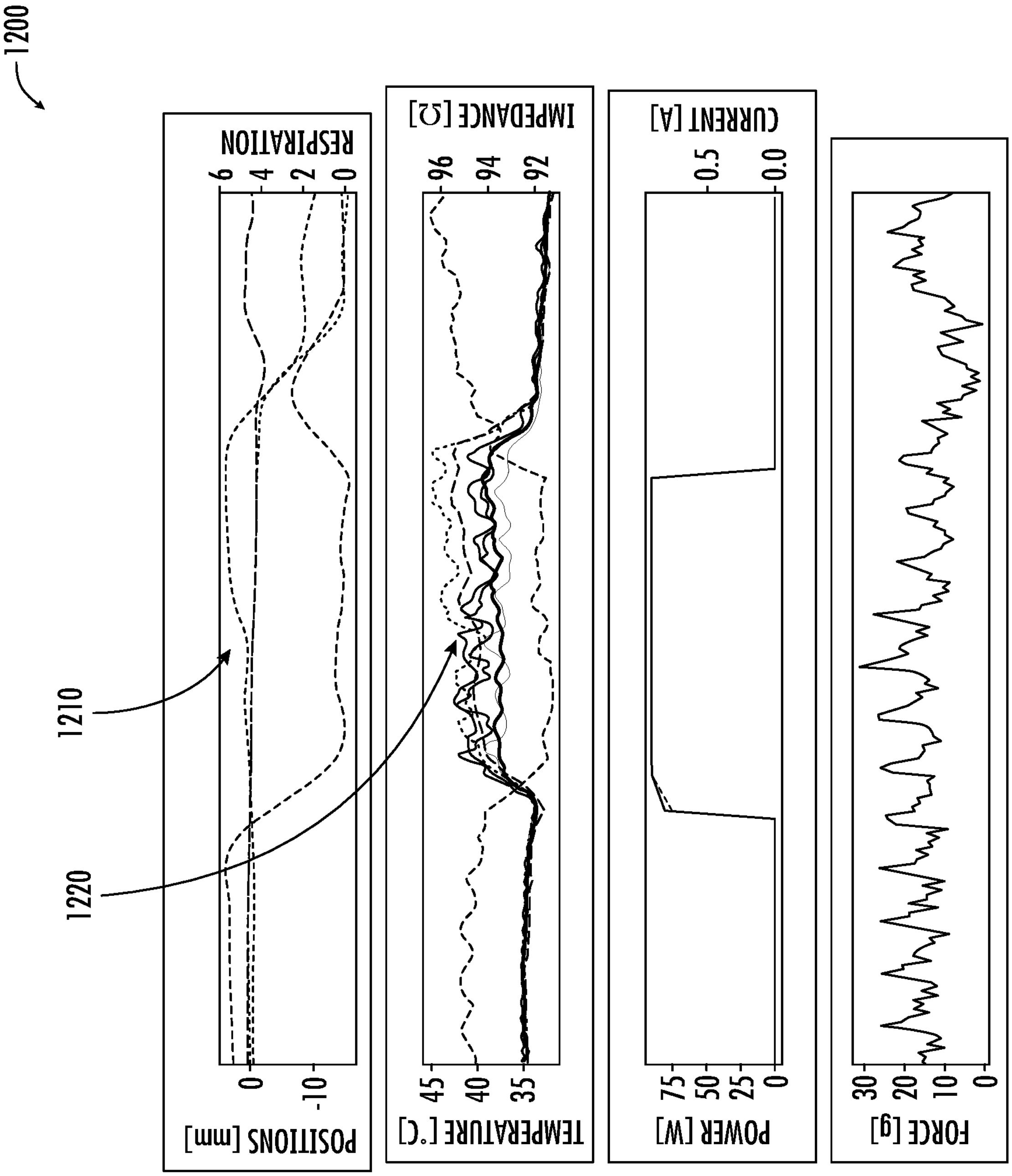

FIG. 12 illustrates a set of graphs 1200 of the parameters of FIG. 9. Set of graphs 1200 indicates that during an ablation procedure a sliding catheter lead to a low stability quality 1210. Specifically, with respect to the location, the first graph of the set provides the curves of the positions indicating a larger variation during the plot. While the force is evidenced as being acceptable in the fourth plot of the sets of graphs 1200, the temperature rise 1220 in the second graph of the set of graphs 1200 is not of good quality, which may be a result of the location stability being poor.

Figure 13:
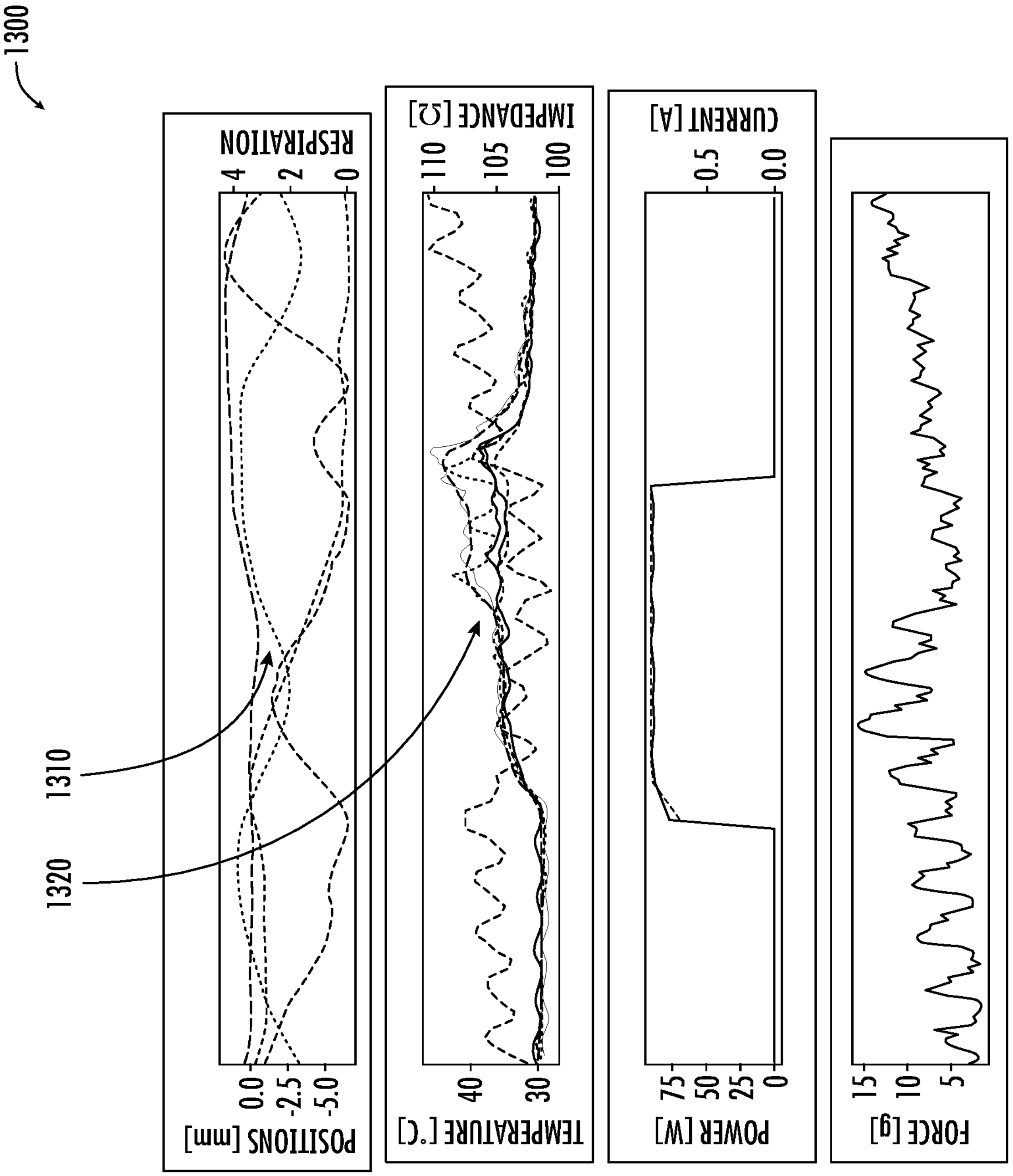

FIG. 13 illustrates a set of graphs 1300 of the parameters of FIG. 9. The force is evidenced as being acceptable in the fourth plot of the sets of graphs 1200. The power and current represent a duration of approximately four seconds in the third graph of the set of graphs 1300. Set of graphs 1300 illustrates that during an ablation procedure there was an adequate average force (fourth graph of set), and an ablation for a duration of 4 seconds (third graph of set), but with an indicated site stability algorithm indicating that only 2.5 seconds of the 4 seconds were stable enough 1310. From this information, even though the ablation was of proper duration, the lesser amount of quality stability for 2.5 seconds is not enough for a successful ablation. This is further illustrated in the effect of the instability on the temperature increases 1320.

Figure 14:
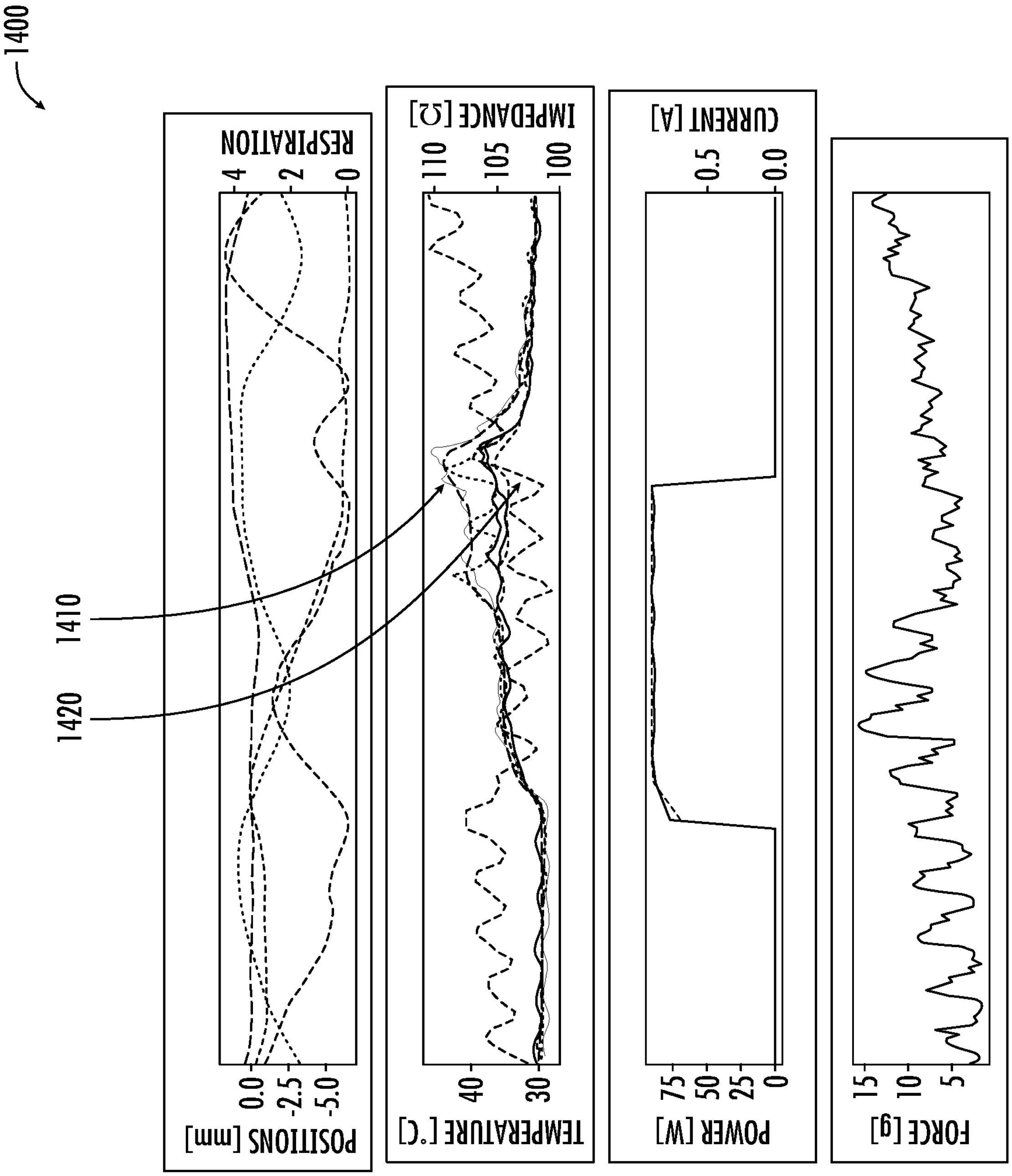

FIG. 14 illustrates a set of graphs 1400 of the parameters of FIG. 9. Set of graphs 1400 illustrates that during an ablation procedure a stable location (within thresholds) and a stable contact force. Specifically, with respect to the location, the first graph of the set provides the curves of the positions indicating a small variation during the plot of a few millimeters. The force is evidenced as being acceptable in the fourth plot of the sets of graphs 1400. The temperature drops 1410 and impedance rises 1420 illustrated in the second graph of the set of graphs 1400. This temperature drop and impedance rise may indicate that the ablation is not heating the same spot on the tissue.

FIGS. 9-14 illustrate the relationships between the various site parameters, in and among the various parameters of AI, T, QS, and DS. As would be understood other parameters may also be used.

In particular, in FIG. 11 the graphs indicates that the ablation duration of 4 sec can be overruled using other parameters to arrive at a real (or effective time of) 2.5 sec ablation—which is below time required for an ablation. This "second order" is further exemplified in case FIGS. 10 and 14 where the location and force are stable, but the temperature drops and impedance rises indicate the ablation is occurring at a different spot.

A logistic regression may be performed. As would be understood, other analysis and regression described with respect to modeling may be used. Using input of calculated data over a number of variables as described, using a standard, the parameters of significance and their respective weights may be determined to predict the gaps as set forth above.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Although features and elements are described above in particular combinations, one of ordinary skill in the art will appreciate that each feature or element can be used alone or in any combination with the other features and elements. In addition, the methods described herein may be implemented in a computer program, software, or firmware incorporated in a computer-readable medium for execution by a computer or processor. A computer readable medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire Examples of computer-readable media include electrical signals (transmitted over wired or wireless connections) and computer-readable storage media. Examples of computer-readable storage media include, but are not limited to, a register, cache memory, semiconductor memory devices, magnetic media such as internal hard disks and removable disks, magneto-optical media, optical media such as compact disks (CD) and digital versatile disks (DVDs), a random-access memory (RAM), a read-only memory (ROM), an erasable programmable read-only memory (EPROM or Flash memory), a static random-access memory (SRAM), and a memory stick. A processor in association with software may be used to implement a radio frequency transceiver for use in a terminal, base station, or any host computer.

The terminology used herein is for the purpose of describing particular embodiments only and is not intended to be limiting. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one more other features, integers, steps, operations, element components, and/or groups thereof.

The descriptions of the various embodiments herein have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

The invention claimed is:

1. A computer-implemented method comprising:

receiving, by an optimization engine executed by one or more processors, data associated with previously performed ablation procedures, the data including performance metrics for the previously performed ablation procedures;

generating, by the optimization engine, expected outcomes for a plurality of the previously performed ablation procedures based on the received data;

generating, by the optimization engine, one or more success predictions associated with one or more potential ablation procedures utilizing the generated expected outcomes;

performing an ablation selected from the one or more potential ablation procedures and calculating a gap index of the performed ablation, the calculated gap index being a function of an ablation index, an average temperature of the performed ablation, a quality of catheter stability, and a distance to a nearest stable site;

identifying gaps in the performed ablation based on the calculated gap index, the identified gaps at least including potential locations of reconnection; and outputting the calculated gap index of the ablation and the identified gaps.

2. The method of claim 1, wherein performing the ablation includes ablating a series of neighboring locations to produce a ring or line of ablated tissue.

3. The method of claim 1, wherein performing the ablation includes providing a series of one or more ablations to prevent transmission of an electric wave.

4. The method of claim 1, wherein generating the one or more success predictions includes searching for the identified gaps in an ablation ring or ablation line.

5. The method of claim 1, wherein a higher value of the calculated gap index at a location of the performed ablation indicates a higher probability that the location corresponds to one of the identified gaps.

6. The method of claim 1, wherein the ablation index is derived from at least one of force, power or time of the previously performed ablation.

7. The method of claim 1, wherein the quality of catheter stability is derived from a site stability algorithm.

8. The method of claim 1, wherein the distance to the nearest stable site is determined using a site stability algorithm.

9. The method of claim 1, wherein the calculated gap index is calculated for each location of the performed ablation.

10. The method of claim 1, further comprising outputting a map highlighting locations where the calculated gap index exceeds a threshold value.

11. The method of claim 10, wherein the locations where the calculated gap index exceeds the threshold value are determined by thresholding the calculated gap index.

12. A system comprising an input/output (I/O) device for receiving catheter data from a catheter configured to perform ablation on a patient heart;

a memory; and a processor, the memory and the processor configured to process the received catheter data and to:

receive, by an optimization engine executed by one or more processors, procedure data associated with previously performed ablation procedures, the procedure data including performance metrics for the previously performed ablation procedures;

generate, by the optimization engine, expected outcomes for a plurality of the previously performed ablation procedures based on the received procedure data;

generate, by the optimization engine, one or more success predictions associated with one or more potential ablation procedures utilizing the generated expected outcomes;

perform an ablation selected from the one or more potential ablation procedures and calculate a gap index of the performed ablation, the calculated gap index being a function of an ablation index, an average temperature of the performed ablation, a quality of catheter stability, and a distance to a nearest stable site;

identify gaps in the performed ablation based on the calculated gap index, the identified gaps at least including potential locations of reconnection; and output the calculated gap index of the ablation and the identified gaps.

13. The system of claim 12, wherein performing the ablation includes ablating a series of neighboring locations to produce a ring or line of ablated tissue.

14. The system of claim 12, wherein performing the ablation includes performing a series of one or more ablations to prevent transmission of an electric wave.

15. The system of claim 12, wherein the generated one or more success predictions is based on searching for the identified gaps in an ablation ring or ablation line.

16. The system of claim 12, wherein a higher value of the calculated gap index at a location of the performed ablation indicates a higher probability that the location corresponds to one of the identified gaps.

17. The method of claim 12, wherein the ablation index is derived from at least one of force, power or time of the previously performed ablation.

18. The method of claim 12, wherein the quality of catheter stability is derived from a site stability algorithm.

19. The method of claim 12, wherein the distance to the nearest stable site is determined using a site stability algorithm.

20. The system of claim 12, wherein the calculated gap index is calculated for each location of the performed ablation.

21. The system of claim 12, further comprising outputting a map highlighting locations where the calculated gap index exceeds a threshold value.

22. The system of claim 21, wherein the locations where the calculated gap index exceeds the threshold value are determined by thresholding the calculated gap index.

* * * * *